United States Patent [19]

Ulitzur et al.

[11] Patent Number: 4,861,709

[45] Date of Patent: Aug. 29, 1989

[54] DETECTION AND/OR IDENTIFICATION OF MICROORGANISMS IN A TEST SAMPLE USING BIOLUMINESCENCE OR OTHER EXOGENOUS GENETICALLY-INTRODUCED MARKER

[75] Inventors: Shimon Y. Ulitzur; Jonathan C. Kuhn, both of Haifa, Israel

[73] Assignee: Technicon Research A.G., Chur, Switzerland

[21] Appl. No.: 739,957

[22] Filed: May 31, 1985

[51] Int. Cl.$^4$ .......................... C12Q 1/68; C12Q 1/66; C12Q 1/02; C12Q 1/04
[52] U.S. Cl. .......................................... 435/6; 435/5; 435/8; 435/14; 435/18; 435/19; 435/21; 435/25; 435/26; 435/29; 435/32; 435/34; 435/36; 435/38; 435/170; 435/172.1; 435/261; 435/822; 935/52; 935/55; 935/56; 935/57; 935/58; 935/79; 935/80; 935/82
[58] Field of Search .................. 435/5, 6, 8, 29, 32, 435/36, 34, 38, 39, 170, 172.1, 261, 14, 18, 19, 21, 25, 26, 42, 822, 828, 832, 842, 843, 848, 849, 851, 852, 863, 870, 871, 873, 874, 879, 880, 885, 909, 948; 935/52, 55-58, 60, 72, 79, 80, 82

[56] References Cited

U.S. PATENT DOCUMENTS 4,038,143  7/1977  Juni .............................. 435/172.3 X
4,540,667  9/1985  Orser et al. ........................... 935/60
4,581,335  4/1986  Baldwin ............................... 935/60

OTHER PUBLICATIONS

Engebrecht, J. et al., Cell, 32: 773–781 (1983).
Belas, R., et al Science 218: 791–793 (1982).
Maniatis, T. in "Molecular Cloning a Laboratory Manual", (Cold Spring Harbor publishers, New York) pp. 17–25 and 38–39 (1982).

*Primary Examiner*—Robert J. Warden
*Assistant Examiner*—Jack Spiegel
*Attorney, Agent, or Firm*—Jeffrey M. Greenman

[57] ABSTRACT

A method for determining the presence of microorganisms in a tests sample. Exogenous DNA containing a luminescent system or other genetic marker system derived from a suitable donor source is introduced by genetic means into a host microorganism which lacks or poorly expresses the donor DNA and whose presence it is desired to detect. Expression of the donor gene system allows the detection of the host microorganism. Compositions of bacteriophages and plasmids as well as a method for detection of antibiotics in a test sample are described.

18 Claims, 11 Drawing Sheets

λ CHARON 30
MAP OF RELEVANT RESTRICTION ENDONUCLEASE CLEAVAGE SITES

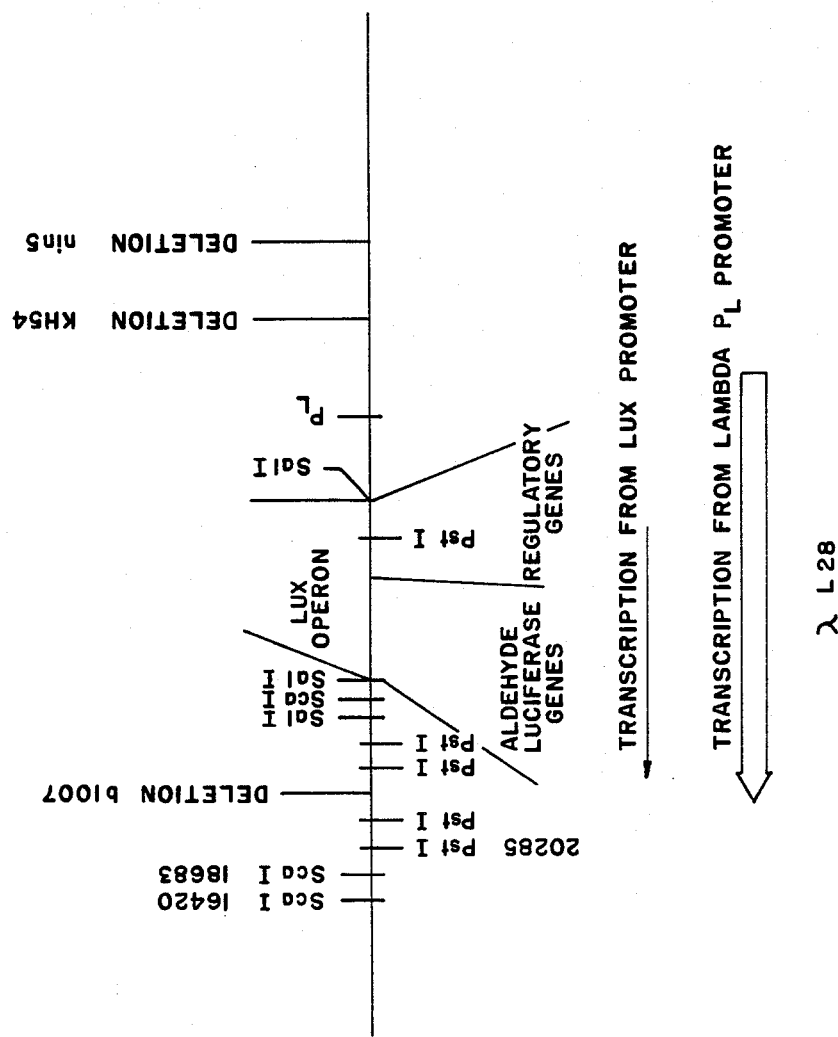

DETECTION AND/OR IDENTIFICATION OF MICROORGANISMS IN A TEST SAMPLE USING BIOLUMINESCENCE OR OTHER EXOGENOUS GENETICALLY-INTRODUCED MARKER

FIELD OF INVENTION

The invention herein described concerns analytical methods, test means, compositions, and methods of preparation thereof for detecting the presence of bacteria in a test sample. Principally, the invention pertains to the determination of bacteria in areas related to health care, such as in the analysis of human excretory products or body fluids, (i.e., urine, blood, feces) for the purpose of aiding diagnosis, or to detect bacterial contamination in foodstuffs. In these and other fields it is important to rapidly, accurately and economically detect the presence of specific bacteria.

DESCRIPTION OF THE PRIOR ART

There are many tests for determining the presence of bacteria and identifying their type. The fast majority are based on the growth of bacterial cultures isolated from sample material containing unidentified bacteria. The specie or species of bacteria that propagate themselves on a selective medium are then isolated and typed by microscopy, physiological tests, sensitivity to antibiotics, uptakes of various stains, serology, etc. Many biological maaterials, such as for example food or skin, contain many king of bacteria. Most such organisms are not of central interest in respect to the aim of the tests (e.g., toxin production, pathogens, etc.). Therefore, most tests employ media that are as selective as possible and which allow the growth of bacteria whose presence is to be determined while trying to prevent the growth of as many as possible of those kinds of bacteria that are not of interest. Examples of such enrichment media are MacConkey for enteric bacteria and thioglycollate broth for anaerobic organisms.

By their very nature these tests are slow because the relevant organism must be isolated before it can be identified and checked for its antibiotic sensitivities. These steps may take as much as several days and this period can be critical in regard to bacterial diseases of humans and animals.

Enumeration and identification of microorganisms as well as the determination of their susceptibility to antibiotics are the main goals of diagnostic medical microbiology. Numerous techniques, tests and media have been developed in order to achieve these goals. However, none of the currently applied tests allow the fulfillment of these tasks by a short-term (i.e., minutes or hours) procedure. A total viable count of bacteria requires 18-24 hrs using present state of the art methods. The estimation of microbial biomass through the determination of adenosine triphosphate (ATP) content is not specific and does not allow the detection of less than $10^{4-5}$ bacteria per ml. Enumeration of a specific species of bacteria usually requires selective media and long periods of incubation. The final identification of the isolated colonies and the determination of their antibiotic susceptibility often requires another cycle of growth and additional tests. Thus, the complete procedure for enumeration, identification and determination of antibiotic susceptibility of bacteria normally requires several days. In contrast, to the more lengthy procedures currently available, modern medicine has long sought rapid diagnostic tools that would allow the rapid determination of the presence and identification of the bacteria causing an infection as well as information on their susceptibility to different antibiotics in a matter of minutes or hours.

A wide variety of alternative techniques have been investigated and developed in the continuing attempt to devise methods which overcome the numerous drawbacks of the conventional culture approach. Light microscopy is used to detect bacteria in clinical specimens and can be used to differentiate between the major groups of bacteria This technique however does not discriminate between dead and living bacteria and the detection limit is usually above $10^7$ cells/ml. Immunological methods have been successfully developed to detect specific species and genera which have surface antigens which are distinguishable by specific antibody binding, but such procedures require a relatively high concentration of bacteria and strain specific antibodies.

Other tests have been developed based on detection of metabolic products of bacteria such as nitrites, nucleotides such as adenosine triphosphate, $^{14}CO_2$ released from $^{14}C$-labelled substrates, and specific. enzymes. The disadvantages of these techniques are many and include: ATP can be degraded by enzymes in the test sample, ATP can originate from nonbacterial sources such as tissues of the host, radioactive materials present a biohazard, and enzymes with similar activity can arise from the host.

Particle counting instrumentation has also been applied to detection of bacteria. Such instrumentation measures perturbations in an electrical current across a small orifice caused by the presence of particles in a fluid flowing through the orifice. Besides requiring the use of a complex and expensive apparatus, this method is highly nonspecific and requires a high level of care and particle-free conditions.

Other types of instrumentation measure the growth of bacteria in special liquid media. The instruments involved make periodic turbidimetric measurements of increases in turbidity indicating the presence of growing bacteria. Here again the method is non-specific and requires a high concentration ($\geq 10^7$ cells/ml) of the bacteria in question.

In light of the foregoing summary of some demands and limitations of conventional microbiology, there ia a continuing, long-felt need for a rapid, sensitive, accurate and economical technique and means for the specific quantitative determination of living bacteria in the milieu in question. Despite the rapid advance of salytical techniques in closely related fields, as represented by the development of the radioimmunoassay, spectrophotometry, fluorometry, microcalorimetry, and electrochemical techniques, the predominant technique used in bacteriological testing remains plate culture. This technique today still involves many of the same materials and methods used by Pasteur and other early microbiologists of the 20th century.

Among biological systems, genetic recombination ordinarily does not occur between unrelated species of organisms. However, the new recombinant DNA technologies now permit the transfer of genes between related or unrelated organisms. The possibility of genetic alteration of gene structure has particular application in the fields of industrial and medical microbiology. Diverse genetic information can now be gathered in vitro from various prokaryotic and eukaryotic sources in the form of DNA fragments and introduced into selfreplicating genetic moieties known as cloning vectors. Alternatively, DNA fragments, or even intact genes, can be constructed by synthetic chemical means to correspond to desired theoretical or known genetic sequences and then introduced into a selected vector. Bacterial plasmids or bacteriophages are commonly used cloning vectors. Plasmids are autonomous extrachromosomal genetic units consisting of circular strands of DNA which are found in most bacteria and some eukaryotes. Bacteriophages are DNA viruses which parasitize only bacteria. Hybrid genetic vectors can then be introduced into selected microbial hosts, which in turn serve as potential factories for the production of large amounts of the cloned DNA.

Transformed microorganisms often do not express the foreign genetic information present in the cloning vector. Such non-expressing cloning vectors are desirable in those situations where expression of the foreign genome could produce a product deleterious to the host organism. A non-expressing or low-expressing cloning vector represents a ready source of the foreign genetic material which can then be isolated and introduced in turn into a suitable expression vector (i.e., a specially prepared or selected plasmid). By use of techniques known to the art, the foreign DNA is placed in a suitable location in an expression vector where the indigenous genetic sequence is such that the foreign genetic information will be transcribed (i.e., mRNA produced from the foreign DNA) and translated (i.e., protein synthesis from the mRNA template) and the desired product coded in the foreign DNA obtained. Transformed microorganisms containing such expression vectors serve as factories for the manufacture of the foreign-DNA product.

DNA can be cut in vitro at specific locations in preparaation for insertion into an appropriate transfer vector by use of a class of enzymes known as restriction endonucleases. Restriction endonucleases are site-specific endonucleases which primarily cleave double-stranded DNA, but in some instances cleave single-stranded DNA. For example, Class II restriction endonucleases cleave at specific sequences. In contrast, Class I restriction endonucleases appear to cleave DNA randomly and produce heterogeneous products Various restriction endonucleases produce DNA fragments of different lengths and types. For example, some restriction endonucleases cleave both DNA strands at the same point and produce the so-called "blunt end" DNA fragments. In contrast, other restriction endonucleases cleave one DNA strand several nucleotides away from the cleavage on the complimentary strand and produce "cohesive end" DNA fragments. Consequently, an accomplished practitioner of the recombinant DNA art can, by creative selection of endonucleases for treatment of subject DNA, obtain desired DNA fragments which can then be joined together by the action of a DNA ligase. For ligation purposes, it may be desirable to add nucleotides to the ends of cut DNA fragments and to add complementary deoxyribonucleotides to the ends of the cloning vector (i.e., in the process known as homopolymeric tailing). Another general method for obtaining a desired DNA fusion product is the addition of "adapter" or "linker fragments" to the ends of either or both the cloning vector or the DNA fragments to be cloned. Linker fragments are small sections of DNA that contain one or more recognition sequences for restriction endonucleases. Thus, the cutting and splicing of DNA containing genetic information is accomplished. The exact sequences of foreign DNA which has been cloned and inserted into a host microorganism can be determined by DNA sequencing procedures.

Foreign DNA material can be obtained for insertion into a transfer vector by several ways. For example, DNA fragments directly obtained from the parental source can be inserted into the appropriate vector. Another method is to obtain mRNA from an active synthesis location in the parent system and to then enzymatically synthesize (reverse transcriptase) a single-stranded complementary DNA strand from the isolated mRNA. A double-stranded DNA molecule is then synthesized from the single-stranded template Double-stranded DNA obtained in this fashion is known as complementary DNA (cDNA). Once a desired DNA sequence is known, genes can also be chemically synthesized in vitro for cloning/expression purposes in microbial, tissue, or cell culture systems.

During recent years there has been dramatic progress in the area of molecular biology due to the advent of recombinant DNA technology. Some of these efforts have been directed towards diagnostic tests. Various inherited disorders can be detected in human embryos, for example, and even the carrier state can be uncovered in parents not showing the disorder itself through the use of restriction endonucleases and nucleic acid hybridization techniques. The ascertainment of the presence of a given type of bacterium using DNA or RNA specific probes and nucleic acid hybridization technology is also under development. However, the use of novel genetic constructs, especially those made partly or wholly by artificial means (in vitro) to detect the presence of specific organisms has not been reported and is the basis of the present invention. A preferred embodiment of the invention employs the luminescent system from *Virbio fischeri*. The technique we have developed is by no means limited to that system. Any exogenous genetically-introduced system showing marked increase of expression in host bacteria whose presence or absence is to be determined can also be used.

The literature is replete with publications concerning bioluminescence and chemiluminescence (c.f., *Bioluminescence in Action*, P. J. Herring, ed., Academic Press, New York, NY 1978; *Bioluminescence and Chemiluminescence*, M. A. de Luca and W. D. McElroy, eds., Academic Press, New York, NY, 1981). U.S. Pat. Nos. 3,958,938; 3,470,373; 3,567,581; 3,959,081; 3,567,586; and 4,144,134 relate to phosphorescence and chemiluminescence.

The literature treating various aspects of genetic engineering, and more particularly concerning recombinant DNA, is rapidly evolving. Various patents have issued in the area related to vectors, recombinant compositions, methodology, and novel microorganisms. Examples of such Patents are: U.S. Pat. Nos. 4,082,613; 4,184,917; 4,190,495; 4,195,125; 4,237,224; 4,468,464; 4,259,444; 4,262,090; 4,262,731; 4,273,874; 4,259,444; 4,262,090; 4,262,731; 4,273,874; 4,321,365; 4,399,216; 4,340,674; 4,506,013; 4,503,151; and 4,504,584. U.S. Pat. No. 3,930,956 involves the transfer of raw bacterial DNA to an auxotroph. The detection of phage-induced lysis of bacteria is described in U.S. Pat. No. 4,104,126.

In 1983 Engebrecht et al. (J. Engebrecht, K. Nealson and M. Silverman 1983, Bacterial Bioluminescence: Isolation and genetic analysis of functions from *Vibrio Fischeri*, Cell 32:773-781) described a variety of recombinant plasmids constructed by ligating BamHl restriction fragments of *Vibrio fischeri* (MJ-1) DNA with the plasmid PACYC184. These recombinant plasmids were introduced into E. coli where they expressed and produced luminescence at a level comparable to that of *Vibrio fischeri*. Additional publications concerning bacterial luminescence include: Belas, R. et al. Sci. 218:791-3 (1982); Evans, J. F., et al. In vitro synthesis of subunits of bacterial luciferase in an *Escherichia coli* system. J Bacteriol. 153:543-545( 1983); Engebrecht, J. and M. bacterial bioluminescenece. Proc. Natl. Acad. Sci. USA, 81:4154-4158 (1984); Engebrecht, J., et al. Measuring gene expression with light. Sci. 227:1345-47 (1985). Luminescent systems not involving luciferase are known [DeSole, P., et al.,J. Clin. Lab. Automation 3: 391-400 (1983)]. In these publications there is no mention of making use of this technique for the determination of bacteria; nor to the best of the inventors' knowledge is the use of luminescing genetic elements for the determination of bacteria or other microorganisms suggested in any other publication.

It is the object of the present invention to provide a short-term test that allows the specific identification of bacteria. It is a further object of the invention to provide a highly sensitive test capable of detecting and identifying bacteria in low concentration. It is still a further object of the invention to provide such a test that enables a quantitative estimation of the determined bacteria. It is yet another object of the invention to provide a test for the determination of the susceptibility of bacteria to antibiotics. These and further objects are manifest in the following description and particularly delineated in the appended claims.

GENERAL BACKGROUND OF THE INVENTION

Various plants and animals exhibit biological chemiluminescence. Bioluminescence is found in microorganisms [i.e., some bacteria (mostly marine forms, e.g., *Vibrio fischeri*), fungi, and dinoflagellates], insects (e.g., the firefly, *Photinus pyradis*), some crustaceans (i.e., *Cypridine hilgendorfi*), jellyfish, worms and other invertebrates and even in mammals. Although the biochemical mechanism of luminescence is known to vary (i.e., the luminescence system found in bacteria is different from that found in fireflies and dinoflagellates), light production in living organisms is most frequently catalyzed by the enzyme luciferase. Bacterial luciferase is a mixed function oxidase, consisting of two different subunits each with a molecular weight of approximately 40,000 daltons.

In the bacterium *Vibrio fischeri*, the synthesis of the enzymes participating in the luminescenece system is regulated by a small sensory molecule, named autoinducer. During growth the autoinducer is accumulated in the growth medium. When the autoinducer reaches a critical concentration, induction of the luminescence system occurs, resulting in approximately 1000 fold increase in light production.

The preferred element of the new test is a fragment of DNA carrying the luminescence system of a luminescent bacterium, usually a marine bacterium, e.g., *Vibrio fischeri*.

An extracellular DNA fragment carrying the luminescence genes does not, of course, luminesce but upon transferring it to a suitable living host by transduction or transformation, the host's genetic and synthetic machinery can utilize the DNA fragment thereby causing light to be emitted. Intracellular gene segments can also be used if in the test organisms they are poorly expressed or unexpressed and only become expressed after some genetic transfer of exogenous DNA to the organism whose presence or absence is to be determined. This latter method employs conjugation, i.e., mating and genetic transfer from one cell to another.

The introduction of DNA into a bacterial cell by bacteriophage infection (transduction), by transformation or by conjugation, is usually limited with respect to the donor source: DNA transfer occurs among a group of strains of the same species or among closely related species. Some factors acting to limit such transfer include the presence of DNA restriction-modification systems in many bacterial species and/or their strains, the dependence on host factors for the replication of the introduced DNA and appropriate bacteriophage receptors in the bacterial wall upon which bacteriophage can adsorb and thereby properly inject their genetic material into the host.

Conjugation and transformation are not particularly strain specific. Some plasmids can be transferred by conjugation not only to the same species but also to related ones. There are even several plasmids which can be transferred to distant species by conjugation. Transformation is potentially even broader than conjugation since a wide range of bacteria take up extracellular DNA. Many, if not most, that are at present not known to do so may in fact be transformable under specific conditions. For example, *E. coli* does not normally take up DNA efficiently. However, after calcium shock this bacterium can be induced to do so at a high level of efficiency. A limiting factor in using transformation is the ability of the foreign DNA to express, replicate or integrate its genetic information into the host genome.

Unlike transformation and conjugation, transduction is quite strain or species specific. Some bacteriophages infect several species of bacteria which are usually close relatives; most infect only a particular subset of strains of a single species. By using different kinds of strains of bacteriophage which infect subsets, it is possible to arrange the strains of a bacterial species into classification schemes. This is called phage typing.

Recombinant DNA technology and molecular genetics allow the introduction of genes whose products are easily assayable. Thus, the introduction of a gene such as lac z of *Escherichia coli* into a bacterium can lead to expression of the introduced gene. If for example a bacteriophage is used to introduce the gene, then the course of the subsequent infection can be measured by analyzing the extent of beta-galactosidase formation. Even though the bacterial cell itself may possess a gene for this enzyme, these measurements can be performed because the endogenous level can be depressed by appropriate media and the propagation of the bacteriophage genetic material leads to multiple copies of the gene.

Although numerous exogenous genetic systems may be utilized in the invention, the luminescent system of *Vibrio fischeri* is particularly useful and illustrative of our method for ascertaining the presence or absence of a given bacterial species. Only a few bacterial species contain genes allowing them to convert chemical energy to light. Most of these species are marine. The vast majority of bacterial species do not contain such systems and are dark. If the genes for light production are introduced and express themselves in a species with no such capability, then emission of light will result. The background interference in such a system is extremely low (chemical luminescence). Since very low levels of light can be detected and measured, tests based on this method should be sensitive and quantitative.

SUMMARY OF THE INVENTION

In accordance with the invention, there are provided methods and compositions useful for the determination of a specific type or group of bacteria in a milieu wherein exogenous DNA containing a luminescence system or other genetic system derived from a suitable donor organism is transferred by transformation, transduction, or conjugation (genetic means) to a host organism lacking or containing relatively low levels of endogenous DNA. The entry of the donor genetic material into the organism which it is desired to determine leads to the expression of the introduced system. The expression of such genes allows one to detect the Presence and numbers of such organisms. In addition, if antibiotics are added at the time of entry, the susceptibility of the host organism to the antibiotic can be determined. A preferred embodiment of the invention involves the transference of a luminescent system, or part thereof, obtained from a luminescent bacterium (or other source), and used as a source for transferring this system into a non-luminescent host microorganism with subsequent expression of luciferase or other system in the host and concomitant production of light or other marker. The invention can also be used to detect antibiotics in a test sample, to assay microorganisms for antibiotic susceptibility, or to assay compositions for antibiotic activity.

Alternatively, any other genetic system which is absent or poorly expressed until entry into the bacteria whose presence it is desired to ascertain may be used. For example, introduction of genes coding for enzymes or proteins (e.g. beta-galactosidase of *E. coli* or the egg albumin protein from chickens) whose expression can be monitored by enzymatic assay, or by immunoassay can be used. These measurements may be based on changes in pH or changes in ion concentration for species other than $H^+$; for the production of a specific molecule (e.g., amino acid, base, lipid, etc.) or the degradation and disappearance of a specific molecule; the production of gas (e.g., $H_2$ by *E. coli*); the formation or disappearance of color (e.g., p-nitrophenol from p-nitrophenyl phosphate by alkaline phosphatase) or a molecule with particular light absorption properties at given wavelengths or radioactively labelled molecules; the production or disappearance of secondary molecules dependent on primary products.

Luminescent bacteria are mainly marine, a typical example being *Vibrio fischeri*. The DNA containing a luminescence system derived from a luminescent bacterium, firefly, dinoflagellate, or luminescent fungi, etc. may be natural, in which case it is derived as such from the luminescent organism. Alternatively, the DNA containing a luminescence system or part thereof derived from a luminescent bacterium or other source may be an artificial recombinant or synthesized DNA with the luminescence system or part thereof being derived from the luminescent source.

In cases involving a bacterial luminescence system, it may be desirable to include in the medium an amount of autoinducer of the luminescent bacterium from which the luminescence system or part thereof is derived, in order to avoid any prolonged incubation time which would otherwise be required for the formation of the autoinducer inside the host organism. If desired, it is also possible to add an aliphatic aldehyde to the milieu in order to accelerate or increase the expression of the luminescence system or part thereof derived from a luminescent bacterium. In those instances where a foreign genetic marker system other than a luminescence system is introduced into a suitable host, it may be advantageous to introduce intermediates, precursors, enzymatic substrates, or other ingredients to facilitate or enhance expression of the marker genetic system or detection of the expression.

In the host organism the DNA containing a luminescence system or part thereof derived from a luminescent bacterium or other source is transcribed by RNA polymerase to form mRNA that can then be translated into the luminescence system proteins. The luminescence level of even a single bacterium can be detected with, for example, the aid of a scintillation counter.

It is thus seen that, in accordance with the invention, luminescence is produced upon interaction between two non-luminescent components, namely the organism to be determined and said DNA containing a luminescence system or parts thereof derived from a luminescent bacterium or other source. Consequently, any luminescence that exceeds the weak background chemiluminescence is conclusive of the presence of the host organism. Conversely, the absence of any luminescence beyond the background level of chemiluminescence is conclusive of the absence of the host organism. Such a technique has never been suggested before.

It is possible, in accordance with the invention, to construct standard curves showing, for example, the correlation between the level of luminescence or other expressed system and the concentration of the bacteria in question. Using such curves the amount of bacteria in the milieu can be closely approximated.

The transfer of the DNA containing a luminescence or other marker system or parts thereof derived from a suitable donor to the host organism may be mediated by transformation, transduction or conjugation. A large number of microbial genera serve as hosts for bacteriophages and retain or accept plasmids. Examples of such genera are: Escherichia, Aerobacter, Salmonella, Shigella, Klebsiella, Proteus, Pseudomonas, Staphylococcus, Streptococcus, Chlamydia, Mycoplasma, Pneumococcus, Neisseria, Clostridium, Bacillus, Corynebacterium, Mycobacterium, Camphybacter, Vibrio, Serratia, Enterobacter, Providencia, Chromobacterium, Brucella, Yersinia, Haemophilus and Bordetella.

For transduction bacteriphages are constructed that are specific to the bacteria to be determined. If desired, a series of test may be run each with a different bacteriophage, either sequentially or simultaneously.

Some bacteriophages may be constructed by packaging DNA containing a luminescence system or parts thereof or other donor marker system derived from a luminescent bacterium or other suitable source in the proper bacteriophage capsid. Alternatively, the bacteriophage may be constructed by recombinant DNA technology using restriction endonuclease with or without subsequent packaging. Alternatively, the bacteriophages containing all or part of the luminescence or other system may be constructed through naturally occurring genetic recombinational mechanism. This can also involve the use of both artificial recombination and natural recombination.

For conjugation the invention provides bacterial strains containing a luminescence system or parts thereof in a transferable replicon. The replicon may be the bacterial chromosome or a plasmid. The luminescence system or parts thereof may be introduced by a bacteriophage or by genetic recombination, either natural or artificial, such that the luminescence genes are covalently linked to the transferred genetic material. Alternatively, any other genetic system whose primary or secondary products can be measured as described earlier can be used in a like fashion. For the sake of illustration, luminescence is given as a relevant and particular example of the more general principle underlying this invention.

For example, it is possible to use for conjugation in accordance with the invention, bacterial strains that are Hfr's (high frequency of conjugation), and which are lysogenic for a temperate bacteriophage carrying the luminescence system. Obviously other Hfr's or donors can be made through genetic recombination, either natural or artificial, or through the addition of genetic material such that the Hfr or donor carries the luminescence system or parts thereof.

In the performance of a test according to the invention herein described, the host organisms perform metabolic activities that are involved in the formation of luminescence or other donor systems; this includes protein synthesis and a process that generates a reducing power. Antimicrobial agents that affect these processes or alter cell integrity abolish or reduce the formation of the donor genetic system (i.e., luminescence, etc.). Consequently it is possible in accordance with the invention to determine the susceptibility of bacteria to various antibacterial agents, e.g., antibiotics. To this end the specific type or group of bacteria to be tested are subjected to DNA transfer as specified in the presence of a given antibacterial agent, and the kinetics of the expressed donor genetic system (i.e., luminescence), which are a function of the protein synthesis capacity and the general metabolism of the host bacteria are then determined. Preferably simultaneous tests are run, one in the absence of any antibacterial agent and several others each in the presence of a particular antibacterial agent. By comparing the results of such tests conclusions can be drawn on the susceptibility of the tested bacteria to any of the tested antibacterial agents.

DESCRIPTION OF SPECIFIC EMBODIMENTS

Materials and Methods

Figure 1:
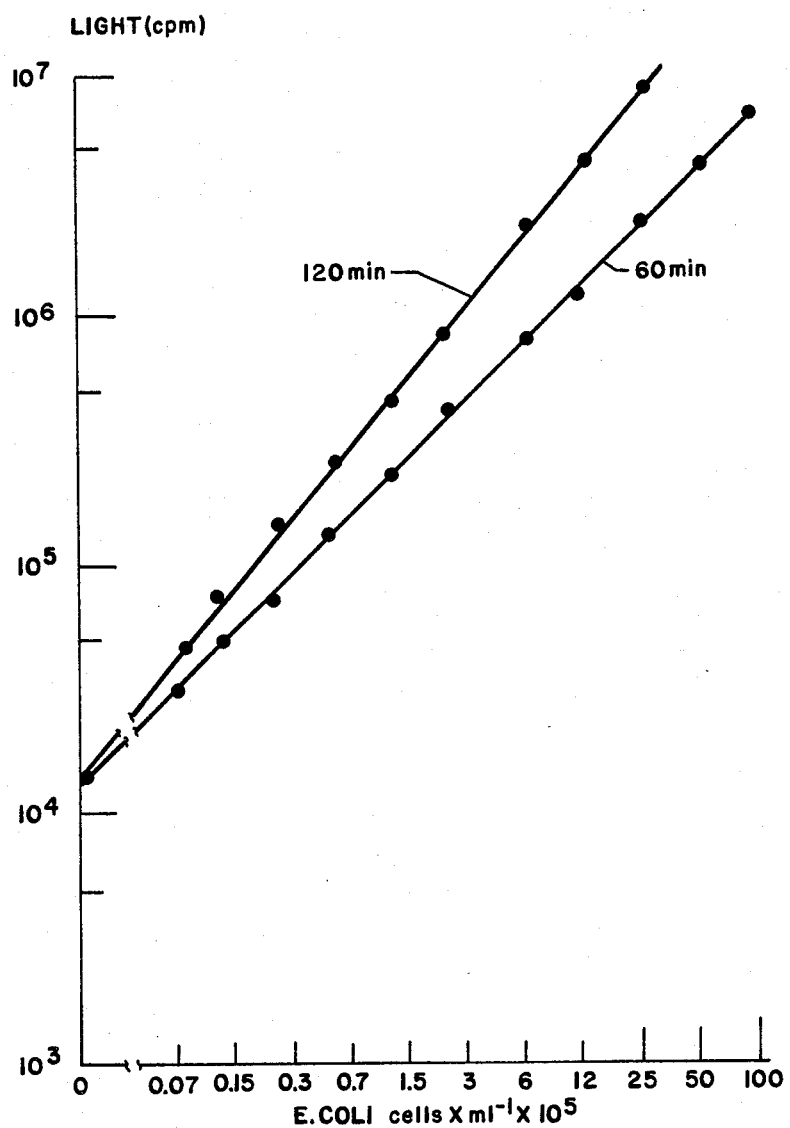

I. Growth media
  A. LB (Lennox broth). (Lennox, E. S. 1955, Transduction of linked genetic characters of the host by bacteriophage. Pl. Virology 1:190-206). [10 g tryptone; 5 g NaCl; 5 g yeast extract; 1 l distilled $H_2O$; 4 ml 1N NaOH]
    1. For petri dishes: 15 g/l agar is added.
    2. Autoclaved at 121° C. for 15 minutes.
    3. As additions where indicated: (a) ampicillin 30 mg/l; (b) chloramphenicol 30 mg/l; (c) tetracycline 15 mg/l.
  B. FT [10 g tryptone; 5 g NaCl; 2 g maltose; 10 ml 1M $MgSO_4$; 1 l distilled $H_2O$]
    1. Autoclaved at 121° C. for 15 minutes.
    2. As additions where indicated: (a) ampicillin 30 mg/l; (b) chloramphenicol 30 mg/l; (c) tetracycline 15 mg/l.
  C. T for bacteriophage [10 g tryptone; 5 g NaCl; 10 g agar; 1 l $H_2O$]
    1. Autoclaved 121° C for 15 minutes.
  D. TA (Top Agar) [10 g tryptone; 5 g NaCl; 6.5 g agar; 1 l $H_2O$]
    1. Autoclaved 121° C. for 15 minutes.
  E. Complex liquid medium (ASWRP) and the complex solid medium are described by Ulitzur et al. (Ulitzur, S., Weiser, I. and S. Yannai 1980: A new, sensitive and simple bioluminescence test for mutagenic compounds. Mutation Res. 74:113-124).

II. Strains and DNA
  A. Bacterial strains
    1. MM294 *E. coli* K12 endA thi pro hsdR (Backman, K., Ptashne, M. and W. Gilbert, 1976: Construction of plasmids carrying the cI gene of bacteriophage. Proc. Natl. Acad. Sci. USA 73:4174-4178.
    2. JM101 *E. coli* K12 endA thi sbcB supE lacpro/F'traD proAB lacI lac z ΔAM15 (Vieira, J. and J. Messing, 1982: The pUC plasmids, an M13mp7-derived system for insertion mutagenesis and sequencing with synthetic universal primers. Gene 19:259-268).
    3. W3110 *E. coli* K12 F⁻ wild type (Yanofsky, C., Horn, V., Bonner, M. and S. Stasiowski, 1971: Polarity and enzyme functions in mutants of the first three genes of the tryptophan operon of *Escherichia coli*. Genetics 69:409-433).
    4. AT2448 *E. coli* K12 HfrH met.
    5. CSHI *Escherichia coli* K12 lac trp strA (Miller, J. H. 1972: Experiments in Molecular Genetics. Cold Spring Harbor Laboratory, Cold Spring Harbor, N.Y.)
    6. *Proteus vulgaris*.
    7. *Staphylococcus albus*.
    8. *Aerobacter aerogenes* 62-1 (Gibson, F., 1968: Chorismic acid, P. 94-97. In W.E.M. Lands, (ed.), Biochemical preparations, vol. 12. John Wiley and Sons, Inc., New York).
  B. Bacteriophage strains
    1. λ cI+ wild type.
    2. λ Charon 30 (Maniatis, T., Fritsch, E. F. and J. Sambrook, 1982: Molecular Cloning. Cold Spring Harbor Laboratory, Cold Spring Harbor, N.Y.).
    3. λ cI857 S7 (Miller, J. H., 1972: Experiments in Molecular Genetics. Cold Spring Harbor Laboratory, Cold Spring Harbor, N.Y.).
    4. λ cI⁻b2.
    5. λ cI857 S7 plac5 (Miller, op. cit )
  C. Plasmids and DNA
    1. pBR322 4.36 Kb, containing genes for resistance to ampicillin and tetracycline (Bolivar, F., Rodriguez, R. L., Greene, P. J., Betlach, M. C., Heynecker, H. L., Boyer, H. W., Crosa, J. H., and Falkow, S., 1977: Construction and characterization of new cloning vehicles. II. A multipurpose cloning system. Gene 2:95-113). After transformation, these resistances are convenient for detecting the presence of the plasmid or recombinants of them.
    2. pACYC184 A plasmid of 4.3 kb containing genes for resistance to tetracycline and chloramphenicol (Chang, A. C. Y., and Cohen, S. N., 1978: Construction and characterization of amplifiable multicopy DNA cloning vehicles derived from the P15A cryptic miniplasmid, J. Bacteriol. 134:1141–1156).

III. Bacteriophage techniques

In the main the techniques described by Miller (loc. cit.) were used except that the medium for plates was T and the liquid medium was FT.

IV. Preparation of bacterial DNA

The method of Marmur was used (Marmur, J. 1961: A procedure for the isolation of deoxyribonucleic acid from microorganism. J. Molec. Biol. 3:208–218).

V. Use and source of restriction endonucleases

Restriction endonucleases were purchased from BRL, New England Biolabs, Boehringer and Amersham. Digestion of DNA by such enzymes was according to the suggestion of New England Biolabs catalogue (1982) except that 100 µg/ml gelatin replaced bovine serum albumin in all cases. DNA concentration did not exceed 2 µg/20 ul.

A. Agarose gels
1. 2 g agarose (Sigma catalogue No. A6013).
2. 200 ml TAE buffer (1X); TAE buffer 10X: (a) 48.4 g Sigma 7-9 Tris (hydroxymethyl aminomethane) catalogue No. T1378 (Tris HCl); (b) 27.2 g sodium acetate; (c) 10.5 g NaCl; (d) 7.5 g disodium ethyelene disinetetraacetic acid; (e) 17 ml concentrated HCl; (f) 925 ml H$_2$O distilled; (g) pH 8.2 at 25° C;
   (i) To each sample of DNA (1–20 l) was added 4 µl of bromophenol blue in glycerol.
   (ii) The gels were run under buffer at 40–250 mA until the dye had run an appropriate distance.
3. Where necessary, cI857 S7 DNA was cut with restriction endonuclease HindIII or EcoRI and used as a molecular size standard. Regression analysis was used to establish the relation between the log of the molecular length and migration distance. The standard was considered acceptable when the correlation coefficient was greater than r=0.99.
4. The gels were stained by placing them in plastic trays with sufficient water to cover them. Seven drops of ethidium bromide (Sigma E8751) at a concentration of 10 mg/ml were added and dispersed by gentle tilting of the pan. After 15 minutes the excess dye was removed by suction, the gel rinsed with water and covered again with water without dye. After 15 minutes the water was removed and the DNA visualized by placing the gel on a long wave UV light box. Photographs were taken with Kodak Tri X pan Professional Film.

VI. Ligation

DNA's digested by restriction endonucleases were precipitated by the addition of one-tenth volume of 3N sodium acetate and 2.2 volumes of distilled 96% ethanol. After freezing at −70° C.in a dry ice-ethanol bath, the Eppendorf tubes were centrifuged for 10 minutes in an Eppendorf centrifuge, the supernate carefully removed and discarded, the pellet washed with 100 µl 1 70% ethanol, centrifuged for 3 minutes, the supernate removed and discarded, and the pellet dried for minutes in a dessicator under vacuum. The dry pellets were resuspended in water.

Ligations were performed in 20 µl containing 4 µl of a five-fold concentrated kinase-linker buffer (Maniatis et al., loc. cit.) and 1 µl of DNA ligase (New England Biolabs., Catalogue No. 202; 400 units/ml) at 25° C. for 12–16 hours. The DNA concentration was usually 0.5–1.0 µg/20 µl reaction.

VII. Preparation of plasmid DNA

A. Preparation of crude plasmid DNA from small volumes
1. The bacterial strain containing a plasmid is grown overnight at 37° C. in LB medium containing an antibiotic to which the plasmid confers resistance so that only bacteria with the particular plasmid reproduce.
2. 1 ml of the cell suspension is centrifuged for 20 seconds in an Eppendorf centrifuge.
3. The supernate is discarded and the cell pellet resuspended in 50 µl of STET buffer (8% sucrose, 5% Triton-100, 50 mM disodium ethylenediamine tetraacetic acid, 50 mM Tris (hydroxymethyl aminomethane)-HCl, pH 8.0).
4. 4 µl of 10 mg/ml lysozyme (Sigma, catalogue No. L6876) is added.
5. The suspension is immersed in boiling water for 40 seconds.
6. The suspension is immediately centrifuged in an Eppendorf Centrifuge, model 5412, for 20 minutes.
7. The supernate is carefully removed to a fresh tube, the pellet is discarded.
8. 50 µl of isopropanol are added and the contents mixed. The tube is placed at −70° C. for 10 minutes in an ethanol dry-ice bath.
9. The tube is centrifuged for 10 minutes in the Eppendorf centrifuge.
10. The supernate is removed and discarded. The pellet is dried under vacuum for 5 minutes.
11. The pellet is resuspended with 50 µl of 0.3 M sodium acetate.
12. 150 µl of distilled ethanol are added, the contents mixed and the tube placed at −70° C. in the ethanol dry-ice bath for 10 minutes.
13. The tubes are centrifuged for 10 minutes, the supernate carefully removed and discarded.
14. The pellet is rinsed by adding 200 Ul of cold (−20° C.) 70% ethanol without disturbing the pellet.
15. The tube is centrifuged for 2 minutes, the supernate removed and discarded, and the pellet dried under vacuum for 10 minutes.
16. The pellet is resuspended with 20 µl of H$_2$O.
17. For most plasmids about 1 µg of fairly pure plasmid DNA is recovered.

B. Preparation of highly purified plasmid DNA by cesium chloride-ethidium bromide equilibrium density-gradient centrifugation.
1. Grow a 1 liter culture for 12–16 hrs in LB medium with an appropriate antibiotic so that only those bacteria breed which contain the particular plasmid.
2. Chill and centrifuge at 5000 xg for 10 minutes at 0° C. in four 250 ml centrifuge bottles. Discard the supernate.
3. Wash the pellet with 20 ml of Tris-HCl buffer pH 7.9, 25 mM containing 1 mM ethylenediaminetetraacetic acid (EDTA).
4. Resuspend each pellet in 7.5 ml of 25% sucrose made up in 50 mM Tris-HCl pH 8.0 and transfer each resuspended pellet to a 40 ml polypropylene tube (Oak Ridge type).
5. Add 1.5 ml lysozyme (Sigma catalogue No. L6876). The lysozyme is made fresh at 5 mg/ml in 0.25 M Tris-HCl pH 8.0. Mix and hold for 5 minutes at 0° C.
6. Add 3 ml of 0.25 M Na EDTA pH 8.0. Mix and hold for 5 minutes at 0° C.
7. Warm to room temperature and add 1 ml of sodium lauryl sulfate (SDS) solution (12.5% in 50 mM Tris-HCl, pH 8.0). Mix gently by inversion and hold for 15 minutes.
8. Chill to 0° C. and add 2.5 ml of 5 M NaCl. Mix gently by inversion and hold for 30 minutes at 0° C.
9. Centrifuge at 43,000 g (19,000 rpm in a Sorvall SS-34 rotor) for 45 minutes at $-4°$ C.
10. Decant the four supernates (12 ml each) into four 40 ml polypropylene tubes. Discard the pellet. Dilute with an equal volume of water.
11. Add to each tube 50 $\mu$l of RNAase A, 10 mg/ml, (Sigma catalogue No. R5503) after inactivation of any DNAase activity through heating in T1 buffer at 80° C. for 20 minutes. T1 buffer is: 10mM $MgS_4$, 0.5 mM $CaCl_2$, 0.1% gelatin, 6 mM Tris-HCl, pH 8.0. Hold at 37° C. for 1 hour.
12. Chill and add 4 ml of phenol that has been saturated with STE buffer. STE buffer is 10 mM Tris-HCl pH 7.9, 10 mM NaCl, 1 mM EDTA. Mix well and centrifuge at 16,000 g for 15 minutes at 0° C.
13. Carefully remove the upper layer (aqueous phase) from each tube into a single 250 ml centrifuge bottle. Add a one-quarter volume of 5 mM NaCl and mix. Add an amount of ethanol that is twice the total volume of the mix. Mix. Hold at $-20°$ C. for at least 12 hours.
14. Centrifuge at 9000 rpm for 45 minutes. Remove and discard the supernate. Add 50 ml of 70% ethanol and gently wash the pellet. Spin 20 minutes at 9000 rpm. Remove and discard the supernate. Drain the pellet and then dry it under vacuum for 15 minutes. Resuspend the pellet in 5 ml of STE buffer.
15. Make the DNA containing solution to 46.2 ml with STE. Add 45 g of CsCl. Add 1.8 ml of ethidium bromide (Sigma, catalogue No. E8751) at 10 mg/ml in STE buffer. Adjust the solution so that its refractive index $r_D$ is between 1.3870-1.3880 ($\rho = 1.565$-1.576).
16. Pipet 10 ml of the mix into each of six $3 \times 5/8$ inch polyallomer tubes. Cap tubes, fill with paraffin oil and centrifuge in a Ti 50 rotor at 38,000 rpm for 48 hours at 15° C.
17. Remove the lower band (viewed with an UV lamp) using a 1 inch 20 gauge needle and a 3 ml syringe. Extract the ethidium bromide 4 times with an equal volume of isopropanol (stock kept over CsCl-saturated STE buffer).
18. Dilute the separate aqueous solution with 4 volumes of water and add twice the total volume of ethanol (96%). Hold for 12 hours at $-20°$ C. Centrifuge in 40 ml polypropylene tubes at 19,000 rpm for 1 hour at $-4°$C. Decant and discard the supernate. Drain the tube and then dry under vacuum for 15 minutes. Resuspend the DNA in 1 ml of STE buffer.

VIII. Transformation (M. Mandel and A. Higa, 1970: Calcium dependent bacteriophage DNA infection, J. Molec. Biol. 53:159-162).

The bacterial strain to be transformed is grown overnight at 37° C. in LB medium. It is diluted 1:200 into fresh LB and grown with aeration at 37° C. until its absorbance, A, at 600 nM is 0.5. The culture (original volume) is chilled on ice, then centrifuged in a Beckman centrifuge at 7000 rpm for 7 minutes at 0° C. in a JA 20 rotor. The cells are resuspended in the same volume of ice cold 0.1 M $MgCl_2$, and centrifuged as before. The cell pellet is resuspended in one-half of the original volume of 0.1 M $CaCl_2$ and kept on ice for 30 minutes. The suspension is centrifuged as before and resuspended in one-tenth of the original volume of 0.1 M $CaCl_2$. These cells are competent for transformation.

A 0.2 ml portion of these concentrated $CaCl_2$ treated cells is mixed with 1-100 $\mu$l of solution containing 0.1-2 $\mu$g of DNA. The mixture is held at 0° C. for 30 minutes, heated to 42° C. for 3 minutes in a water bath and again placed on ice for an additional 20 minutes. Then 0.8 ml of LB medium is added and the culture placed at 37° C. for 1 hour to allow the expression of antibiotic resistance essentially without cell division since the cells are recovering from the calcium shock. Portions of the culture are placed on LB plates (containing the appropriate antibiotics). Controls consist of untransformed but $Ca^{++}$ treated cells and cells transformed with a known amount of an uncleaved plasmid.

IX. Construction of pBTK5 and transformation into MM 294 E. coli.

DNA (8 $\mu$g) from Vibrio fischeri strain MJ1 was cleaved with 30 units of restriction endonuclease SalI for 3 hrs at 37° C. DNA (6 $\mu$g) of plasmid pBR322 was similarly digested. Samples were tested by agarose gel electrophoresis to check that the digestions had gone to near completion. The cleaved DNA's were precipitated with sodium acetate-ethanol and the dry pellets resuspended in $H_2O$. A 2 $\mu$g amount of V. fischeri DNA was ligated to 0.5 g of pBR322 DNA using 400 units of DNA ligase. The reaction was terminated by adding 200 $\mu$l $H_2O$ and 40 $\mu$l STE saturated-phenol. The mixture was vortexed and centrifuged. The supernate was precipitated with sodium acetate-ethanol and the pellet of ligated DNA was resuspended in 40 $\mu$l of $H_2O$.

Strain MM294 was grown and prepared for transformation. The control transformation contained 1 $\mu$g pBR322 DNA (loc. cit.). After transformation the cells were plated on LB plates containing ampicillin. Cells without added DNA gave no colonies. $2.64 \times 10^6$ transformants/$\mu$g pBR322 DNA were obtained in the control transformation. The ligated mixture gave $3.2 \times 10^4$ transformant colonies/$\mu$g bacterial DNA and $6 \times 10^4$ total transformants were obtained. By checking for the insertional inactivation of the tetracycline resistance gene (inserts of foreign DNA inactivate the gene since the SalI site is in this gene) it was found that about 5% of these transformants contain inserts of V. fischeri DNA. Thus about 3000 inserts were obtained. Seven of the colonies were luminescent.

After analysis of the DNA contained by these 7 colonies, one strain containing a plasmid (pBTK5) that has a single insert of approximately 8 Kb and two SalI sites was chosen. These results are in line with those previously described by Engebrecht et al. (loc. cit.).

X. Construction of pAChv-1 and transformation into MM294 E. coli.

CsCl-ethidium bromide purified plasmid pBTK5 DNA from MM294 strain containing this plasmid obtained according to IX above, was digested with restriction endonuclease SalI and a portion was checked by agarose gel electrophoresis. pACYC184 plasmid DNA, similarly prepared, was cleaved by SalI and analyzed as above. After ligation and transformation into MM294 *E. coli* cells, colonies that were resistant to chloramphenicol (from pACYC184) and that gave light (30° C) were analyzed by standard methods. A strain containing a plasmid (pAChv−1) that has the backbone of pACYC184 and the 8 Kb light producing segment inserted in the SalI site of pACYC184 was kept, and placed in permanent deposit (ATCC 53133).

XI. Construction of λL1, λL4, λL5, λL28, λL32, λL35 and λL40.

Bacteriophage λCharon 30 DNA (0.3 μg), purified as described by Maniatis (loc. cit.), was cleaved with restriction endonuclease SalI and ligated to pBTK5 DNA (0.5 μg) obtained according to IX above, similarly cleaved. After ligation the DNA was precipitated by sodium acetate-ethanol, the pellet dried and resuspended in 5 μl H₂O.

Packaging mix for DNA was prepared by the method of B. Hohn as given in Maniatis (loc. cit.). The packaging of the ligated DNA was carried out according to the protocol of Maniatis (loc. cit.) and Plated with MM294 grown to stationary phase in FT medium. Plaques were checked for light production by transferring them to scintillation vials containing 1 ml FT medium, 0.1 ml MM294 grown on FT medium. Individual plaques had been transferred through the use of a Pasteur pipette to 1 ml of 10 mM MgSO₄. A 0.1 ml of this was transferred to a vial.

Phage strains giving light were plaque purified twice, plate lysates were made and the phage preparations stored over several drops of chloroform. These phages were then characterized for light production during infection of strain MM294 growing in FT medium at 27° C. Autoinducer was added to a duplicate vial (Nealson, K.H., Platt, T., and Hastings, J. W.., 1970, Cellular control of the synthesis and activity of the bacterial luminescent system. J. Bacteriol. )04:313-322), λL1, λL35 and λL40 produce light at times considerably later than the others, the light produced is relatively little and the amount of light emitted is greatly increased if the bacteriophage infection takes place in the presence of autoinducer. Phage strains λL4, λL5, λL28 and λL32 produce light within 15-20 minutes after infection, and the amount of light emitted increases with time and reaches a maximum after about one hour. There is no significant effect of autoinducer on the amount of light produced by these phages.

Since the fragment containing the light genes had been cloned from a digest with restriction endonuclease SalI, insertion of this fragment into λ Charon 30 digested with the same enzyme may occur in two different orientations. In one orientation the luciferase and aldehyde genes (Engebrecht op. cit.) are closer to the N gene of λ, while the regulatory genes of the lux operon are closer to the J gene of λ. In this orientation, the transcription of the aldehyde and luciferase genes will depend on transcription from the lux promoter(s) only, since the direction of transcription will be opposite to that of the PL promoter of λ. In this case, autoinducer should and does stimulate light production. λL1, λL35 and λL40 are most likely phages with inserts in this orientation, since their light emmission is greatly stimulated by autoinducer.

The second possible orientation has the regulatory gene of the lux operon nearer the N gene of λ and the aldehyde and luciferase genes to the J gene side. Since the direction of transcription of the aldehyde and luciferase genes is the same as that of the $P_L$ promoter of λ, these genes should be transcribed not only from their own promoter but even more so from $P_L$. Thus, the addition of autoinducer to cultures of bacteria infected by these kind of phages should and does have little or no effect on light production. Two of these phages, λL4 and λL28, have been characterized and the orientation of their insert found to be that which was expected on the basis of the above physiological observations and theoretical considerations. Phage DNA from λL4 and λL28 was prepared as described by Maniatis (op. cit.) using CsCl gradient purified phage as the source of DNA.

Digestion of these DNAs by restriction endonuclease SalI revealed three large fragments after electrophoresis in agarose gel. The two larger bands are the arms of Charon 30 that the necessary for phage propagation. The smallest band of about 8.8 kilobases is identical to a band from pBTK5 cut with the same enzyme. Thus the inserted DNA piece in both phages seems identical to the piece that was originally cloned from *Vibrio fischeri*. The orientation of the insert in λL4 and λL28 was shown by restriction endonuclease cleavage using PstI. λ Charon 30 has the normal sequence until approximately base pair 23616 (Hendrix R. W., Roberts, J. W., Stahl, F. W., and Weisberg, R. A., 1983: *Lambda* II, Cold Spring Harbor Laboratory, Cold Spring Harbor, New York; Appendix II, pp 519–676) and then the deletion b1007 which extends from approximately base pair 23616 to 28312. From base 28312 until base 34449 the sequence is again normal. At base 34449 an earlier sequence repeats itself and this repeat starts with base pair 22346. The repeat continues until base pair 23616 and then is deleted (b1007) until base pair 28312. Starting with this base pair the normal sequence continues until approximately base pair 35384 at which point a second, different type of deletion, KH54, commences and removes DNA until base pair 37925. Then the normal sequence continues until approximately base pair 40502 at which point a third kind of deletion (nin5) removes DNA until base pair 43307. The sequence after this base pair is normal until the DNA end at base pair 48502 (these numbers are given as the normal base pair coordinates of normal bacteriophage λ; see FIG. 9). Thus λ Charon 30 contains 1 duplication and 4 deletions, two of which are identical. The coordinates for various restriction endonuclease cleavage sites (see FIG. 10) in λ Charon 30 are given in Hendrix (op. cit.) Appendix III. They estimate the phage λ Charon 30 to be 46757 base pairs. From published data the phage would seem to be 46331 base pairs. For our purpose this discrepancy is not important.

The pattern of restriction enzyme fragments obtained from PstI cleavage in λCharon 30 can be calculated from the description of its DNA provided above. After removal of the internal SalI fragment and insertion of the lux operon SalI fragment this pattern is, of course, altered. The PstI sites until the base pair 22425 will be identical to normal λ and also λ Charon 30. There will be a fragment in λ Charon 30 of 4888 base pairs generated by the segment between the site at 22425 and 32009 (contains deletion b1007 which removes 4696 base pairs). This fragment will also occur in the "luminescent" phage described here. However, the DNA insert will alter the pattern between the PstI sites at base pair 22425 and the end (normal λ coordinates). After removal of the internal SalI fragment from λ Charon 30, no PstI sites will exist in the DNA from base pair 32256 (the most distal PstI site remaining) and the end of the phage since the PstI site at base pair 37005 is deleted in λ Charon 30 by the KH54 deletion. There is one PstI site in the SalI fragment containing the lux operon and it is situated very near one end (about 200 bp from the end) and in the regulatory region of the operon.

Thus if the PstI site of the lux operon is near the last PstI site in λ, PstI cleavage will generate a small fragment of about 700 base pairs and a large fragment of about 18-19 kilo bases. This would be the expected cleavage pattern for λL1, λL35 and λL40. Conversely, if the PstI site of the lux fragment is toward the distal end of the , then two fragments of about equal size (approximately 9 and 11 kilobase) should result. Cleavage of λL4 and λL28 DNA gave the latter pattern which confirms our hypotheses that the luciferase and aldehyde genes of the lux operon are located towards the proximal end of λ and have the same transcription orientation as transcription from the $P_L$ promoter.

A final question that can be raised about the structure of λL4 and λL28 has to do with their SalI junctions between phage and insert DNA. λ Charon 30 has four SalI sites. These four are divided into 2 pairs. Within each pair of sites, the sites are separated by only 499 base pairs while the distance between pairs is close to 7000 base pairs. When λ Charon 30 was used as a vector and cleaved with SalI restriction endonuclease to generate λL4 and λL28, the fragment between the pairs will be replaced by the lux operon fragment. What is less clear is whether the recombinant phages contain 2, 3, or 4 SalI sites. If there are only 2, then the junction between the lux operon and DNA was at the most proximal and most distal SalI sites of λ. If there are 4 SalI sites then the lux fragment is joined to the two innermost SalI sites of λ Charon 30. Three SalI sites indicate that a pair of SalI sites still exists at one end of the insert and a single SalI site at the other.

The 7Kb (kilobase) internal fragment of λ Charon 30 must always be removed because, if it were not, the addition of the lux operon would lead to a phage DNA molecule that is too long to be packaged. The small (499 base pair) fragment(s) produced when there remain 3 or 4 SalI sites, can be seen on a gel, but one cannot determine whether there are 3 or 4 sites since each pair gives an identically sized fragment. A solution to this problem is afforded by cleavage by restriction endonuclease ScaI, since ScaI cleaves λ DNA between the two SalI sites of a pair. Thus, if one or both of the ScaI sites disappears, there is no or one pair left in the recombinant λ. There is no ScaI site in the lux operon. ScaI cleaves wild type λ at sites 16420, 18683, 25684, 27262 and 32801 base pairs. In λ Charon 30 the sites at 16420 and 18683 exist while the sites at 25684 and 27262 have been deleted. The site at 32801 occurs twice in λ Charon 30 since there are 2 pairs of SalI - sites rather than the single pair in λ wild type. In λ Charon 30 there is a ScaI site at base pair 28391 and at base pair 35819, besides those at 16420 and 18683. Charon 30 gives fragments of 16420, 2263, 9708, 7428 and 10938 base pairs after ScaI digestion. A recombinant phage having the lux operon and only 2 SalI sites remaining, should give fragments of 16420, 2263 and one of about 28000 base pairs after ScaI digestion. The presence of 3 SalI sites will give either a pattern of 16420, 2263, 9708 and approximately 19000 base pairs, or 16420, 2263, approximately 18500 and 10938 base pairs after ScaI digestion, depending on whether the pair of SalI sites still remaining is proximal or distal respectively. The presence of both pairs of SalI sites will yield fragments of 16420, 2263, 9708, approximately 9300 and 10938 base pairs after ScaI cleavage.

The results of analysis by ScaI endonuclease shows that λL4 contains 4 SalI sites while λL28 has 3. λL28 retains the proximal pair of SalI sites and the most distal SalI site from λ Charon 30. This structure of λ wild type, λ Charon 30, λL4 and λL28 are shown diagramatically in FIGS. 9, 10, 11 and 12, respectively.

XII. Construction of an Hfr able to transfer luminescence.

*Escherichia coli* K12 strain AT2446 which is an Hfr was made for the luminescent bacteriophage λL28. This was accomplished by simultaneously infecting AT2446 with λL28 and λcI−. The latter phage is necessary to provide integration functions, the λatt site for integration, and an active repressor gene to allow lysogenization: all three of these are lacking in λL28. Non-lysogenic cells were eliminated by subsequently challenging the cells with λcIb2 which cannot itself lysogenize and which kills non-lysogens. Survivors that give off light, produce phages after induction by UV light, and carry luminescent genes were isolated.

XIII. Bioluminescence determination.

Luminescence in vivo of aliquots placed in scintillation vials was measured by a photomultiplier photometer similar to that described by Mitchell & Hastings (Mitchell, G. W., and Hastings, J. W., 1971: A Stable inexpensive solid state, photomultiplier photometer. Anal. Biochem. 39: 243-250). When the luminescence intensity was below $10^6$ quanta/sec, a scintillation counter (Packard Model 2001), operating without coincidence at the $^3H$ setting at 25° C, was used. The luminescence was expressed in quanta per second by using the Hastings and Weber standard (Hastings, J. W., and G. Weber, 1963: Total quantum flux of isotropic sources. J. Opt. Amer. 53:1410–1415).

XIV. Autoinducer preparation from *V. fischeri* MJ−1.

To prepare cell-free conditional medium containing autoinducer, V. at 22° C. Late logarithmic phase cultures (80-100 Klett units, Filter 66) that are highly luminescent were centrifuged at 10,000 g at ° ° C. for 15 minutes. The supernatant fluid was sterilized by passage through a 0.22 μm pore size membrane filter (Millipore Corp. Bedford, Mass.). These preparations were stored at 4° C. for up to 30 days without loss of activity.

The bioassay for the *V. fischeri* autoinducer was performed using the methods previously described by Nealson (Nealson, K. H., Platt, T., and Hastings, J. W., 1970: Cellular control of the synthesis and activity of the bacterial luminescent system. J. Bacteriol. 104: 313–322).

XV. Assay of beta-galactosidase.

The assay was performed according to Miller (op. cit.) using chloroform and SDS (sodium lauryl sulfate) to permeabilize the cells to o-nitrophenyl galactoside (ONPG).

XVI. Deposition.

Where indicated, constructions (i.e., plasmid and bacteriophage) of the invention have been placed on permanent deposit in the American Type Culture Collection (ATCC), Rockville, MD 20852,U.S.A.

LIST OF FIGURES

Figure 2:
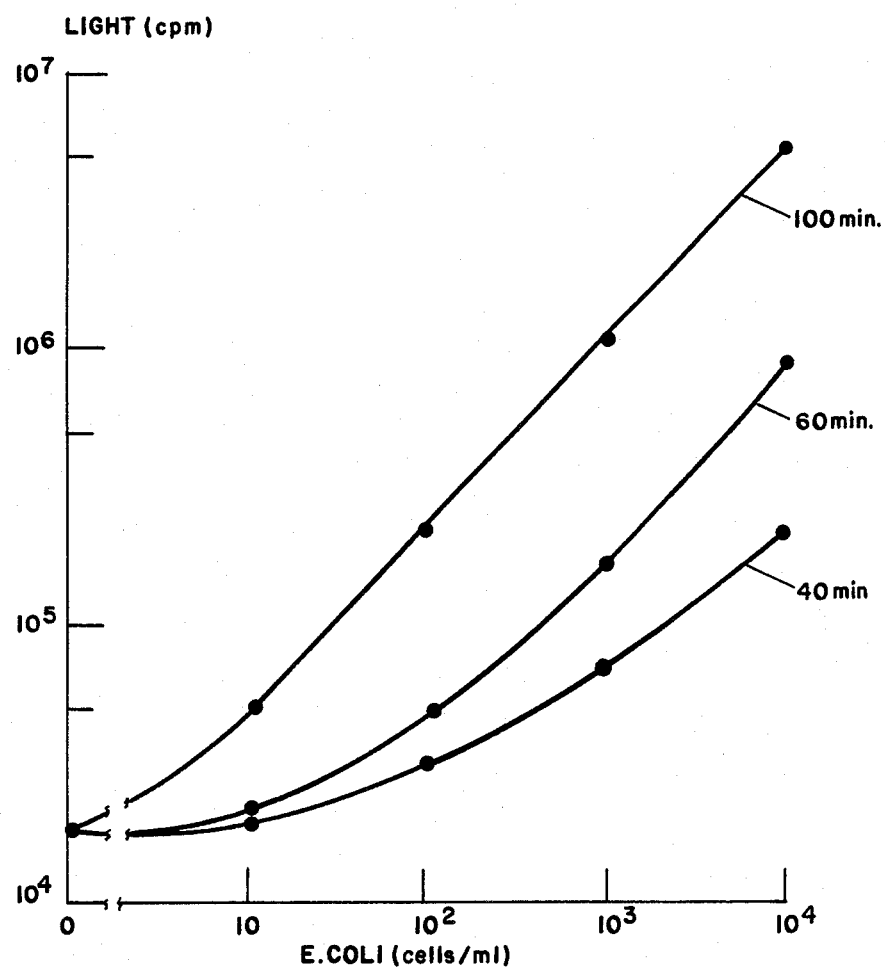
Figure 3:
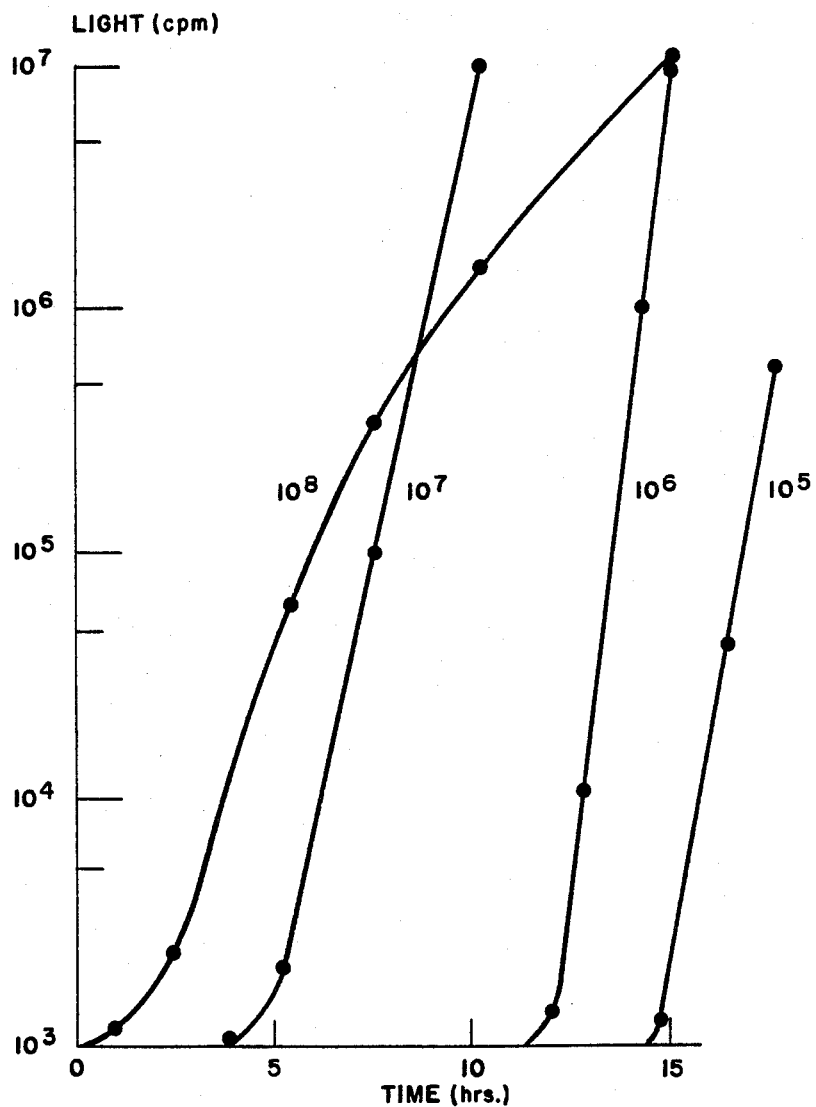
Figure 4:
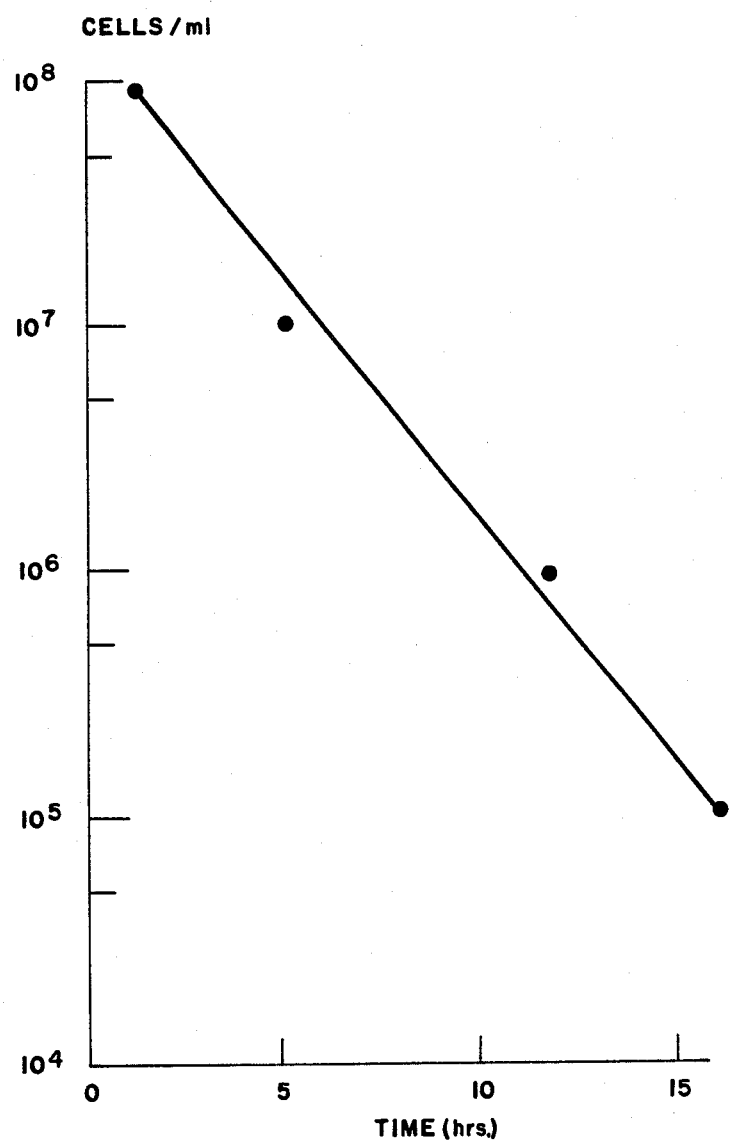
Figure 5:
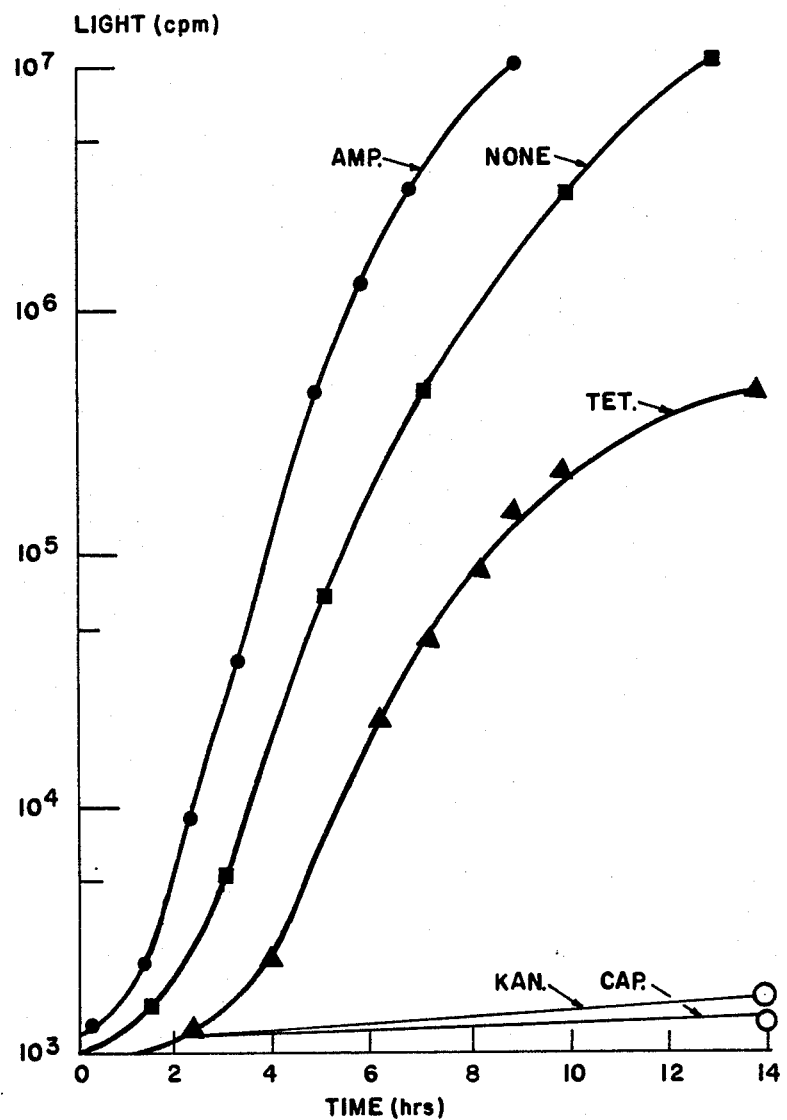
Figure 6:
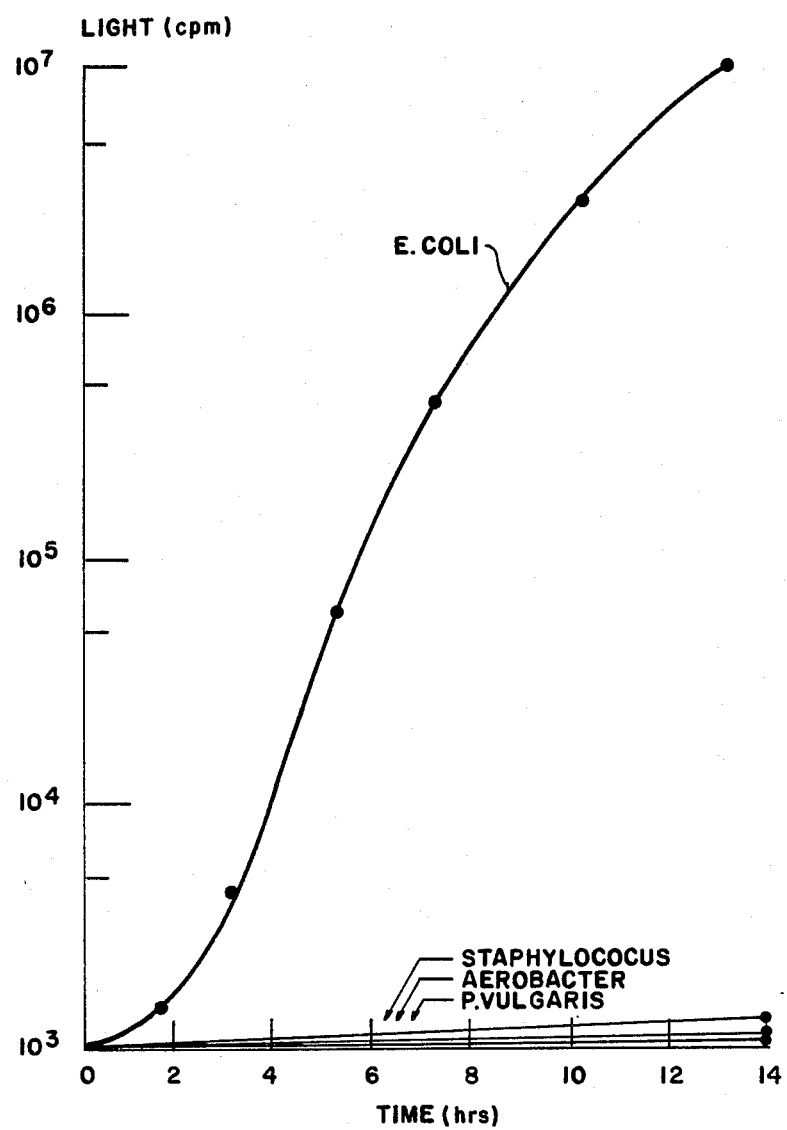
Figure 7:
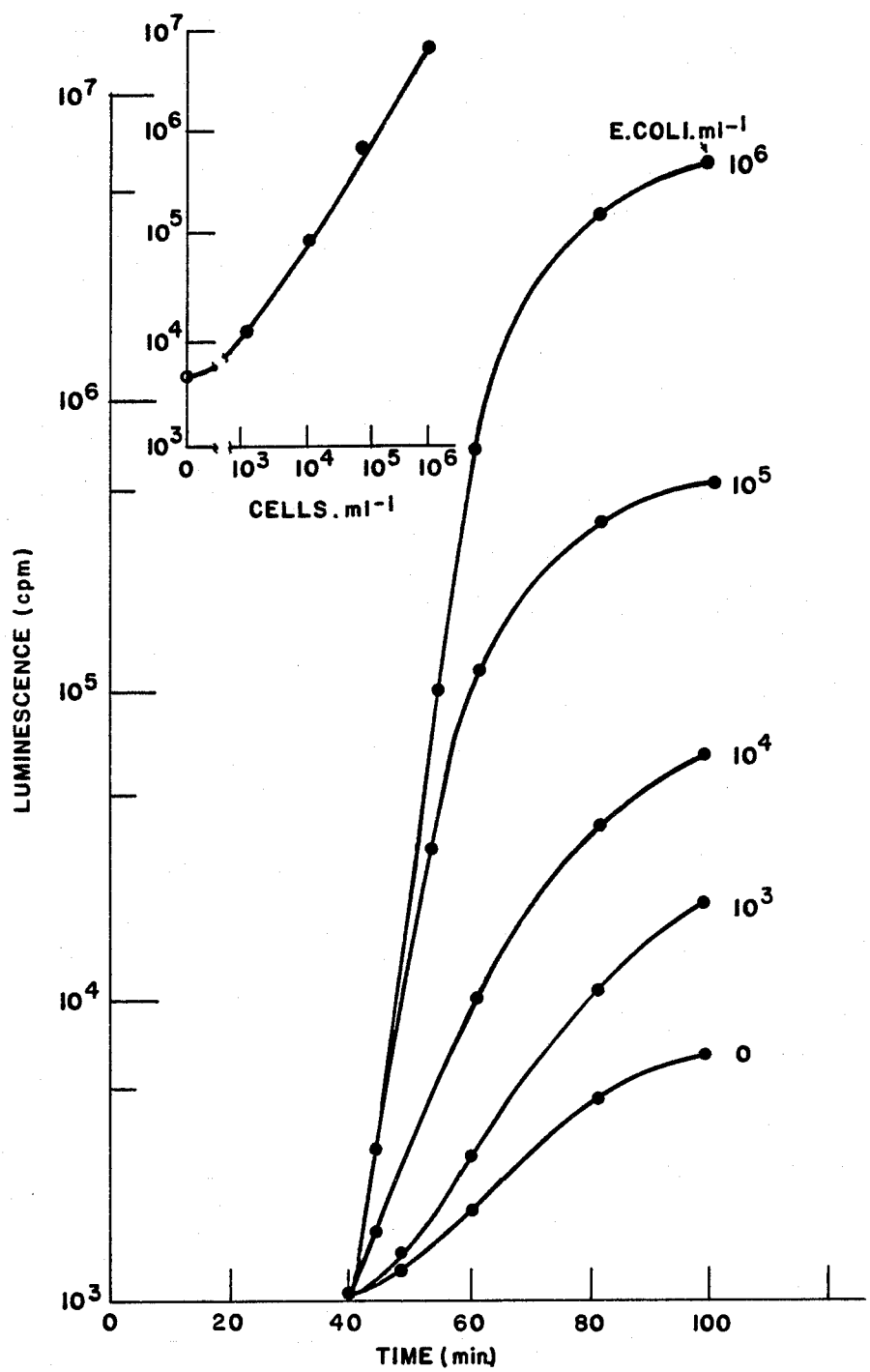

The invention is illustrated in the annexed graphical representations, which show:

FIG. 1—Determination of *E. coli* strain W3110 by transduction with phage λL28;

FIG. 2—Determination of *E. coli* strain W3110 by transduction with phage λL4;

FIG. 3—Determination of *E. coli* K strain MM294 at different concentrations by transformation with 1 μg of pBTK5 DNA;

FIG. 4—The correlation between the cell concentration and the onset of light emission in the determination of E. coli strain MM294 by transformation with 1 μg of pBTK5 DNA;

FIG. 5—The kinetics of luminescence in the transformation of *E. coli* strain MM294 with 1 μg of pBTK5 DNA in the presence of various antibiotics;

FIG. 6 —The specificity of the transformation of *E. coli* strain MM294 with 1 μg of pBTK5 DNA;

FIG. 7—The determination of *E. coli* strain W3110 by conjugation.

Figure 8:
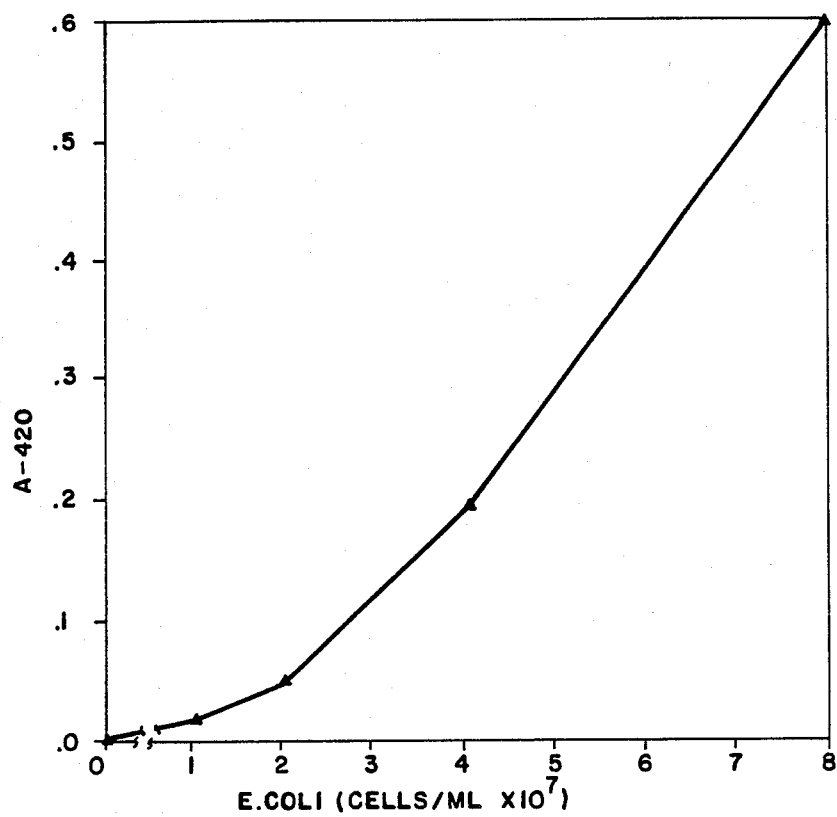
Figure 9:
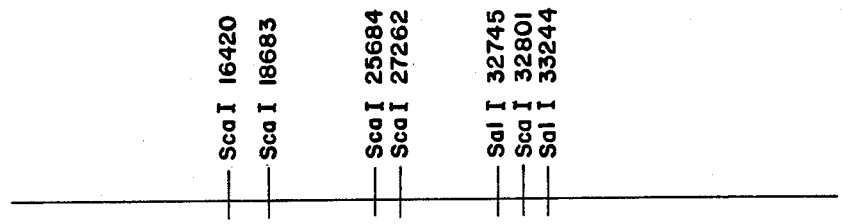
Figure 10:
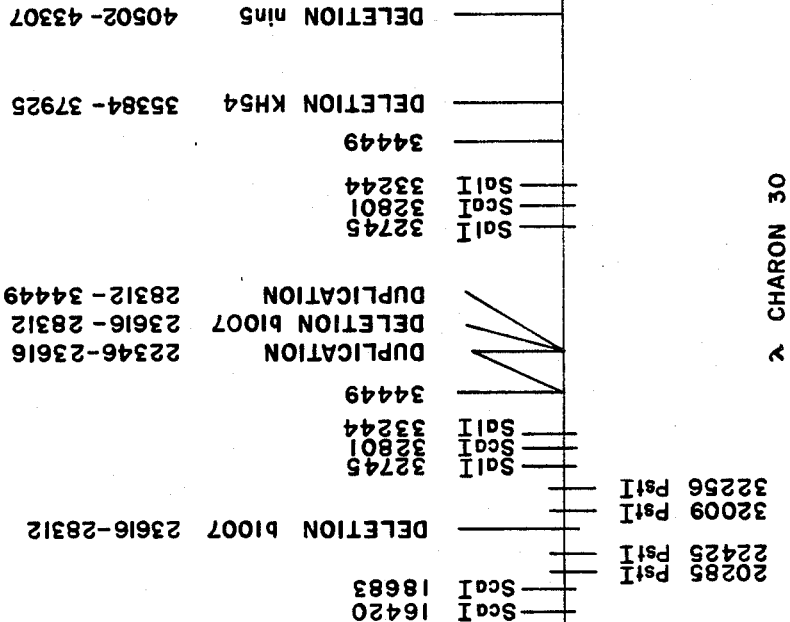
Figure 11:
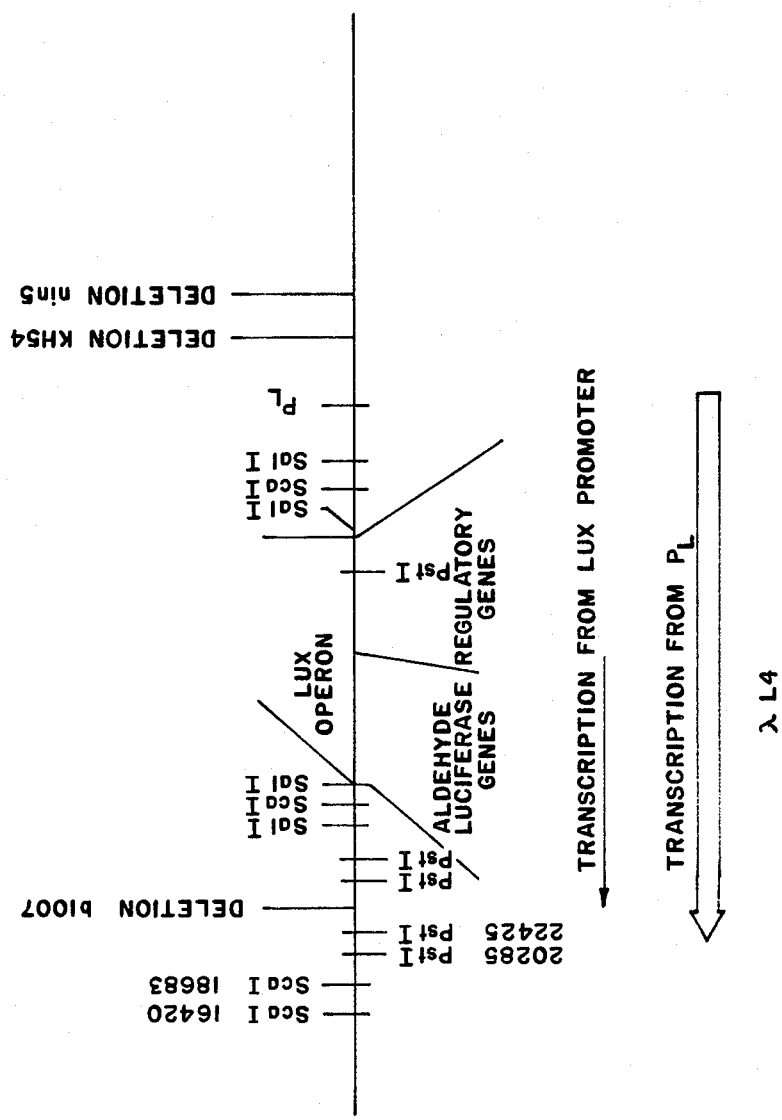

FIG. 8—Determination of *Esherichia coli* strain CSH1 by transduction with λcI857 S7 plac5;

FIG. 9—λ wild type Map of relevant restriction endonuclease cleavage sites;

FIG. 10—λ Charon 30 Map of relevant restriction endonuclease cleavage sites;

FIG. 11—λL4 Map of relevant restriction endonuclease cleavage site, topological features, transcription from lux promoter, and transcription from PL; and FIG. 12—λ L28 Map of relevant restriction endonuclease cleavage site topological features transcription from lux promoter, and transcription from $P_L$.

SPECIFIC EXAMPLES

The invention is further illustrated by the following Examples. These examples are to be considered as models only which demonstrate the general and broad principle of the invention as specified herein, and 20 they are not to be understood or limiting the invention in any way.

EXAMPLE 1

Determination of *Escherichia coli* Strain W3110 by Transduction with Phage λL28

*E. coli* W3110 cells were grown in liquid FT medium to early logarithmic phase of growth at 30° C. The culture was diluted tenfold and duplicate 1 ml samples were transferred to sterile vials. To each vial 25 μl of λL28, 5×10$^9$ PFU/ml (PFU=plaque forming units) was added. The λL28 (ATCC No. 40183) was prepared as described above in Part XI of Materials and Methods. The vials were incubated at 25° C. in the scintillation counter and the luminescence was determined as a function of time as described above in Part XIII of Materials and Methods. FIG. 1 shows the luminescence after 60 and 120 minutes of incubation as a function of *E. coli* concentration. The background count was 15,000 cpm.

EXAMPLE 2

Determination of *Escherichia coli* Strain W3110 by Transduction with Phage λL4

*E. coli* cells were grown 1, in liquid FT medium. The culture was diluted in saline (100 ml) to give final cell concentrations of 10$^1$, 10$^2$, 10$^3$ and 10$^4$ cells/ml. 100 ml of each sample was filtered through 0.45 micron Millipore filters and the filters were placed face upward in sterile scintillation vials. To each vial was added 1 ml of liquid medium containing λL4 at 7×10$^7$ PFU/ml, the λL4 having been prepared as described above in Part XI of Materials and Methods. The luminescence of the vials was determined after 40, 60 and 100 minutes of incubation at 22° C, as described above in Part XIII of Materials and Methods. FIG. 2 shows the relation between the light emission (CPM) and the concentration of *E. coli* cells.

EXAMPLE 3

Determination of *Escherichia coli* Strain CSH1 by Transduction with λcI857 plac5

*Escherichia coli* strain CSH1 was grown with shaking in FT medium at 37° C. Numbers of cells per ml were determined by viable counts on LB plates after a 20 hr incubation at 37° C. Expotentially growing cells were doubly diluted (dilutions of 2) with FT sterile medium. To each vial, isopropyl thiogalactoside (Sigma catalogue number I5502) was added to give a final concentration of 100 mM. λ cI857 S7 plac5 bacteriophage was added to give a final concentration of 10$^9$ plaque forming units/ml. Final volume was 2 ml. The vials were incubated with shaking at 37° C. for 45 min. Then 2 ml of Z buffer (Miller, op. cit.) were added followed by the addition of 0.1 ml chloroform and 0.05ml of SDS (0.1%). The contents of the vial were mixed with the aid of a Vortex mixer (30 sec) and 0.8 ml of ONPG (8 mg/ml) were added to each vial. ONPG was made up in 0.1M sodium phosphate buffer, pH 7.0. The vials were incubated with slight shaking at 37° C. for 60 min. and the reaction was stopped by the addition of 2 ml of Na$_2$CO$_3$ (1M). The developed color was determined with a Bausch and Lomb Spectronic 20 at 420 nm (for o-nitrophenol) and at 550nm for turbidity caused by cellular matter.

FIG. 8 shows the amount of beta-galactosidase formed as determined by enzymatic assay as a function of cell concentration.

EXAMPLE 4

Determination of *Escherichia coli* Strain MM294 by Transduction with pBTK5

Recombinant DNA pBTK5 was prepared from the luminescence system fragment of *Vibrio fischeri* DNA and plasmid pBR322 as described above in Part IX of Materials and Methods. 1 μg of pBTK5 DNA was used to transform different concentrations of E. coli K strain MM294 in 0.2 ml of CaCl$_2$ After transformation, the cells were put in a scintillation vial containing 0.8 ml of LB and 0.2 ml of LB medium containing autoinducer prepared in accordance with Part XIV of Materials and Methods. Cell concentrations in different vials were 10$^5$, 10$^6$, 10$^7$, and 10$^8$ cells/ml. FIG. 3 shows the kinetics of light emission for the four different concentrations of E. coli cells and FIG. 4 shows the correlation between the cell concentration and the onset of light emissions in these experiments. The background light emission was 1000 cpm.

EXAMPLE 5

Determination of *Escherichia coli* Strain MM294 in the Presence of Various Antibiatics Transformation was performed as in Example 3 and the transformed bacteria were subsequently incubated in the presence of various antibiotics. Ampicillin (AMP), 30 μg/ml; chloramphenicol (CAP), 10 μg/ml; kanamycin (KAN), 30 μg/ml and tetracycline (TET), 10 μg/ml. FIG. 5 shows the kinetics of luminescence with and without the antibiotics. The background count emission was 1000 cpm.

EXAMPLE 6

Transformation of Various Bacteria with pBTK5 DNA

Transformation was performed as in Example 3, using as would be recipients *Escherichia coli* strain MM294, *Aerobacter aerogenes* strain 62-1, *Proteus vulgaris* and *Staphylococcus albus*. FIG. 6 shows the level of light emitted (cpm) as a function of time, and it is seen therefrom that only *E. coli* was transformed while the remaining three species remain unaffected. This demonstrates the specificity of transformation with the recombinant DNA pBTK5. The background count was 1000 cpm.

EXAMPLE 7

Determination of *Escherichia coli* Strain W3110 by Conjunction

The HfrH (high frequency of conjugation) strain containing the luminescence gene was constructed as described in XII (Materials and Methods). This strain was grown in LB medium containing streptomycin (2.5 μg/ml) for 2 hrs. at 37° C. The cells were washed once and diluted into LB medium to give a final cell density of $10^7$ cells/ml. To 1 ml aliquots of this culture, different concentrations of (non-luminescent) E. coli strain W3110 cells were added. The mixed cultures were incubated without shaking at 37° C. for 30 minutes and then the cultures were taken for luminescence determinations in a scintillation counter at 24° C. FIG. 7 shows the luminescence developed in the presence of different concentrations of *E. coli* W3110 recipient cells as a function of time (from time zero).

EXAMPLE 8

General Method for the Isolation, Cloning, and Transfer of Exogenous Genes into MICROBIAL Host Organisms, and Detection of the Recipient Host Using the Expression of the Introduced Donor Gene Systems As described previously herein, alternative enzyme or other systems in addition to luciferase and β-galactosidase can be introduced into host organisms for detection purposes in accordance with the invention. The system or enzyme can be chosen because of the ease with which its presence may be determined or because it is unique and absent in the organisms to be ascertained. The luciferase system previously described has both these qualities and is a preferred embodiment of the invention. Genes encoding proteins whose presence can be directly detected by their absorption of light at certain wavelengths (e.g., hemoglobin) or by specific antibodies, radioactively labelled or linked to conveniently determined enzymes (ELISA) or to other compounds such as biotin, can be used for the detection of microorganisms in the ways analogous to detection of luciferase. In other cases, genes encoding enzymes whose product or products can be measured directly or indirectly or in which the disappearance of one of its substrates can be similarly measured may be more suitable. Examples of such enzymes are given below in several Examples. Measurements might be based on evolution of gas or the reduction of the concentration of a dissolved gas, changes in pH, products or substrates that can be directly measured by spectrophotometry or chromatography or indirectly by coupled reactions or by antibody detection of a secondary complex (e.g., biotin-avidin) or through the use of radioactively labelled compounds. Such measurements for identification purposes are given by means of illustration only and are not intended to limit the scope of the present invention, but to indicate the types of systems that might be used in conjunction with our method. Representative enzymes, proteins or enzyme systems can be utilized for detection of microorganisms after the relevant genetic structures have been assembled. Such assembly may involve natural recombination events or in vitro recombinant DNA techniques or both. There are numerous possibilities and strategies consistent with the present invention.

Various isolation, cloning, and transfer procedures involving foreign genes and introduction to host organisms can advantageously be used in the invention. For example, the DNA of donor organisms (i.e., bacterium, yeast, etc.) can be isolated and subjected to partial digestion by the restriction endonuclease Sau3A to yield a set of overlapping fragments encompassing the whole donor genome. Fragments of a particular size may be prepared by centrifugation through glycerol or sucrose gradients or by agarose gel electrophoresis. These fragments contain protruding 5' single strand ends with the structure 5'GATC-double stranded DNA and can then be ligated by T4 DNA ligase to appropriate vector molecules cut with enzymes (BamHI, BglII, BclI Sau3A) that created appropriate and compatible single strand ends. An example of such a vector is λ Charon 28 (Maniatis et al., op. cit.) cut with restriction endonuclease BamHI. The ligated DNA can then be transformed, subsequent to packaging if desired, into an appropriate host (lacking a restriction system). Viral DNA containing sequences for the desired exogenous system or enzyme can be detected either through enzymatic activity, immunological techniques or by synthetic or natural DNA probes and nucleic acid hybridization. Many of the above techniques of cloning and detection are detailed in Maniatis et al. (op. cit.). Subsequently, the donor gene is subcloned and then connected to a powerful bacterial promoter (e.g., plac of *Escherichia coli* or $P_R$ of bacteriophage λ. Then the promoter-gene segment can be transferred by recombination, natural, in vitro or both, to a conjugative plasmid (e.g., F factor or RP4), a transformable element (e.g., plasmid pBR322) or to an appropriate bacteriophage (e.g., λ or T4).

The expressed donor gene or gene system thus transferred to a receptive host microorganism can then be used to identify the host organism. A suitable method for monitoring the activity of the donor genetic system in the host organism is selected (i.e., light production with luciferase; end product or intermediate of enzymatic reaction; gas evolution, etc.). Thus, the isolation, cloning, and transfer of foreign genes from a donor organism into a receptive host microorganism and identification of the host microorganism by monitoring expression of the foreign gene system contained therein is effected.

EXAMPLE 9

Method for the Use of Alcohol Dehydrogenase or Other and Oxidoreductases Gene Systems Obtained from a Foreign Donor and Transferred to a Receptive Host Microorganism for Detection of the Host Alcohol dehydrogenase (E.C. 1.1.1.1; Alcohol:NAD oxidoreductase) is an enzyme that is formed by many species such as yeast, man and Bacillus. The gene or genes coding for this enzyme can be isolated by recombinant DNA techniques. Using the method of Example 8, the DNA of yeast as a donor organism is isolated, treated by restriction endonuclease, cloned, connected to an effective bacterial promotor, and transferred by an appropriate vector, preferably a bacteriophage, to a receptive host microorganism.

The ADH gene can then be used to detect the presence of specific microorganisms by techniques and strategy similar to those presented earlier for bacterial luciferase and beta-galactosidase. In the case of ADH, light production will not be directly monitored; rather the conversion of $NAD^+$ to NADH would be measured. In the presence of ethanol and $NAD^+$, ADH catalyses a reaction whose products are NADH, $H^+$ and acetaldehyde. The presence and concentration of NADH can be determined by adsorbance of light at 340 nm or by bacterial luciferase in the presence of an appropriate aldehyde (e.g., $C_{14}$ aldehyde) (Stanley, P. E. in Methods in Enzymology, volume LVII edited by M. A. DeLuca, Academic Press 1978, New York, San Francisco, London, pp. 215–222).

There are many other NAD oxidoreductases that would be as suitable as ADH (enzymes of E.C. classes 1.1.1, 1.2.1, 1.3.1, 1.4.1, 1.5.1 and 1.8.1) for identification of host microorganisms. For example, L-alanine dehydrogenase (E.C.1.4.1.1., L-alanine: NAD oxidoreductase) also yields NADH from $NAD^+$. In addition enzyme liberates $NH_3$ from L-alanine when it is converted to pyruvate and $NH_3$ may be the product measured rather than NADH. Other oxidoreductases use $O_2$ as the electron acceptor in place of $NAD^+$ (E.C. classes 1.1.3, 1.2.3, 1.3.3 and 1.4.3) and the disappearance of dissolved oxygen might be followed by, for example, an oxygen electrode.

EXAMPLE 10

Method for the use of Genetic Systems Coating for Transferase Obtained from a Foreign Donor and Transferred to a Receptive Host Microorganism for Detection of the Host Transferase enzyme systems can also be used to identify microorganisms in conjunction with the invention herein described. Using the method of Example 8, the DNA of a suitable donor organism containing the selected transferase gene(s) is isolated, treated by restriction endonucleases, cloned, connected to an effective bacterial promotor, and transferred by an appropriate vector (preferably a bacteriophage), to a receptive host microorganism. For example, L-tyrosine:2-oxoglutarate animotransferase (E.C.2.6.1.5) yields P-hydroxyphenylpyruvate from L-tyrosine in the presence of 2-oxoglutarate and the appearance of p-hydroxyphenylpyruvate can be monitored spectrophotometrically at 330 nm (Hadar, R., Slonim, A., and Kuhn, J., 1976. Role of D-tryptophan oxidase in D-tryptophan utilization by *Escherichia coli.* J. Bacteriol. 125:1096–1104). A second example of a transferase is galactokinase (ATP: -D-galactose—1-phosphotransferase; E.C.2.7.1.6) whose activity can be followed by disappearance of ATP or appearance o $\beta$-D-galactose—1-phosphate. Other detection modes can be readily adapted to the particular selected transferase.

EXAMPLE 10

METHOD FOR THE USE OF HYDROLASE, LYASE, OR ISOMERASE GENETIC SYSTEMS OBTAINED FROM A FOREIGN DONOR AND TRANSFERRED TO A RECEPTIVE HOST MICROORGANISM FOR DETECTION OF THE HOST

In addition to the enzyme systems previously described, hydrolase, lyase, and isomerase enzyme systems can be used to identify microorganisms in conjunction with the present invention. Using the method of Example 8, the DNA of a suitable donor organism containing the selected enzyme (hydrolase, lyase, or isomerase) is isolated, treated by restriction endonucleases, cloned, connected to an effective bacterial promotor, and transferred by an appropriate vector (preferably a bacteriophage), to a receptive host microorganism. For example, alkaline phosphatase (E.C.3.1.3.1, orthophosphoric monoester phosphohydrolase) activity can be determined in a number of ways, one of which is by release of P-nitrophenol from p-nitrophenylphosphate. p-nitrophenol concentration can be determined spectrophotometrically at 420 nm at alkaline pH in the same way that o-nitrophenol was used for determination of 8-galactosidase (E.C.3.2.1.23) activity. Lyases such as aspartate—1-decarboxylase (E.C.4.1.1.11, L-aspartate 1-carboxylase) and ornithine decarboxylase (E.C.4.1.1.17, L-ornithine carboxylyase) are equally suitable since the liberation of $CO_2$ (as $H_2CO_3$) can be determined by changes in pH. Isomerases such as glutamate racemase (E.C.5.1.1.3) can also be employed. In the case of glutamate racemase the conversion of D-glutamate to L-glutamate can be followed by coupling the system to L-glutamate oxidase following conventional protocols.

EXAMPLE 12

Method for the Use of Oxidase Genetic Systems Obtained from a Foreign Donor and Transferred to a Receptive Host Microorganism for Detection of the Host The introduction of enzymatic activities into the target host microorganism wherein such enzymatic activity is either low or non-existent. By use of the method of Example 8, the DNA of a suitable donor organism containing the selected enzyme (i.e., oxidase) is isolated, treated by restriction endonucleases, cloned, connected to an effective bacterial promotor, and transferred by an appropriate vector (preferably a bacteriophage imparting specificity) to a receptive host microorganism. One possible use for the present invention involves , for example, D-tryptophan oxidase (Hadar et al., op cit.) which is almost non-existent in *Escherichia coli.* The introduction of the mutant gene leading to high levels of this enzymatic activity is detectable through the production of indolepyruvic acid from D-tryptophan. Likewise elements containing the bio B gene of *E. coli* joined to strong promotor lead to rapid conversion of dethiobiotin to biotin, the latter of which can be detected by methods based on the high affinity of avidin for biotin.

Results

A. Transduction

Bacteriophage propagate themselves by adsorption and subsequent injection of their DNA into an appropriate bacterial host. In nature bacteriophage genes can sometimes become linked to bacterial genes through substitution and/or addition. Occasionally, some bacteriophage envelope accidently DNA coming from a source other than the bacteriophage (i.e. with chromosomal, plasmid or other bacteriophage species). The former is called specialized transduction, the latter generalized transduction. Both of these phenomena lead to the transfer of DNA from one bacterium to another.

A more modern way to produce specialized transducing phages is through the use of recombinant DNA technology. Phages can be constructed that carry desired genes and in which no essential bacteriophage genes have been lost. Such bacteriophages will efficiently introduce these cloned genes if an appropriate host is present. If elements for their expression exist, these genes will be highly expressed since many copies of the bacteriophage chromosome are made during the growth of the phage.

In accordance with a preferred embodiment of the present invention, the fragment of DNA carrying the luminescence genes of *V. fischeri* was transferred to the *Escherichia coli* bacteriophage λ from the plasmid pBTK5. Transference of other donor genetic systems can be similarly effected by appropriate constructions.

Upon infection, the phage adsorb to the specific bacteria capable of acting as host, and the encapsulated DNA of the phage head is injected into the bacterial cell. Once the DNA is inside the bacterium it can make use of the host functions and it is transcribed and translated to produce luminescence enzymes (luciferase and those necessary for aldehyde synthesis) or other introduced enzyme systems.

The use of a luminescent system is a preferred embodiment of the invention. Since neither the phage, nor the bacteria emit light by themselves, the level of light subsequent to infection can be used to detect the presence of bacteria and the amount of light emitted reflects the number of phage-bacterium complexes. In the presence of excess phage the amount of light reflects the concentration of bacteria. Using this technique less than $10^4$ *Escherichia coli* cells/ml can be detected within one hour (FIG. 1). When a sample containing bacteria was concentrated by filtration through Millipore HA 0.45 micron filters, concentrations as low as 10 cells/ml could be detected.

In the presence of an antibiotic to which the host cell is sensitive, the infecting phage cannot complete its lytic cycle and the amount of light emitted is reduced or no light is emitted. Antibiotics that block DNA, RNA or protein synthesis were tested and shown to lower the output of light. Antibiotics that affect cell wall synthesis or membrane integrity gave similar results. Thus, if a given type of bacterium is detected by infection with phage carrying luminescence genes, the susceptibility of the bacterial host to antibiotics can be rapidly determined by examining the effect of an antibiotic on light emission.

The presence of bacteria can also be detected by enzymatic means using transduction as illustrated in FIG. 3. The presence of sufficient bacterial cells and the infection thereof by a bacteriophage carrying a gene coding for beta-galactosidase results in the de novo synthesis of beta-galactosidase whose presence and activity may be determined by enzymatic assay. The greater the number of infected complexes, the greater the amount of enzyme formed.

A similar experiment was performed using a λ bacteriophage carrying the gene for tryptophanase and a bacterial strain deficient for this activity. Again the presence of these bacteria led to enzyme formation, albeit at relatively high concentrations of cells ($10^9$ cells/ml).

Bacteriophage generally can only grow on some or all strains within a given single species of bacteria. Occasionally a given type of bacteriophage can infect several species but these are almost always found to be closely related. By choosing appropriate bacteriophage types, the test for bacteria can be made as specific as desired. This means that not only can the presence of bacteria be detected in this test but also the presence or absence of specific types of bacteria can be rapidly determined. For example, if the detection of *Escherichia coli* is desired, a mixture of phages whose host ranges span all known strains of this species and which carry luminescence genes, would allow the rapid specific detection of this species.

B. Transformation

These experiments illustrate that bacteria can be detected by transforming them with a compatible DNA containing bioluminescence or other donor genes. The presence of bacteria, their approximate numbers, their taxonomic position and their susceptibility to antibiotics can be determined through this technique.

When *Escherichia coli* strains JM101 and MM294 were transformed with plasmids pBTK5 and pAChv−1 obtained, respectively, according to parts IX and X of Materials and Methods, demonstrable light was emitted within a few hours. Cells without added DNA or the DNA alone were totally dark. The level of light emitted was several thousand fold that of the background.

In a separate experiment the amount of light emitted was measured when the added DNA is constant (1 μg) and the cell number varied. The results are shown in FIG. 3 and illustrate that the time of onset of emission is negatively correlated with cell concentration. This is clearly shown in FIG. 4 in which the time of onset of light emission is plotted against cell concentration. The almost linear relationship obtained demonstrates that this method can also be used to approximate cell concentration.

Another application of transformation using light producing genes is in the determination of the susceptibility of bacteria to antibiotics. The plasmid used was pBTK5 (1 μg) and strain MM294. After transformation antibiotics were added and their effect on light emission determined. The experimental controls were $CaCl_2$ treated cells without added plasmid DNA and transformed cells without added antibiotics. FIG. 5 shows the experimental results obtained. Kanamycin (30 μg/ml) and chloramphenicol (30 μg/ml) entirely prevented the production of light. Tetracycline (10 μg/ml) caused a 90% decrease versus that of the control without antibiotic. Ampicillin (30 μg/ml) actually stimulates light production. That ampicillin would not inhibit or only slightly inhibit light emission was expected because pBTK5 caries a determinant for ampicillin resistance. The unexpected stimulation may be due to selection for increased replication of the entering plasmid or to increased transcription of the light genes via the bla gene (ampicillin resistance) promoter. Thus the sensitivity of a bacterial population to an antibiotic (chloramphenicol, tetracycline and kanamycin in these experiments) can be rapidly determined through transformation with bioluminescence genes. Resistance (ampicillin) is also rapidly detected. Furthermore, the activity of an antibiotic can be rapidly ascertained as a function of its concentration (tetracycline versus chloramphenicol and karamycin). A suboptimal concentration or partial resistance is also detected by this test (tetracycline).

An additional feature of transformation is its specificity. As shown above, two strains of Escherichia coli were readily detected. When an experiment was conducted in which Escherichia coli, Proteus vulgaris, Staphylococcus albus and Aerobacter aerogenes were transformed by pBTK5 DNA, only Escherichia coli emitted light (FIG. 6). Since Aerobacter and Proteus are quite closely related to Escherichia coli, this shows that this test has a good deal of specificity.

C. Conjugation

Certain bacteria have the capacity to donate their DNA to other cells (recipients). This process, known as conjugation, is mediated by plasmids which are circular DNA molecules whose presence is often superfluous to the cell's health. Not all plasmids are able to promote conjugation: only those that have transfer genes are able. When the plasmid exists as a free-non-integrated molecule it usually mediates its own transfer from donor to recipient and only occasionally the transfer of other plasmids or of the bacterial chromosome. However, when a conjugating plasmid is integrated into the chromosomes, it primarily transfers the chromosome and only succeeds in transferring itself. The range of possible recipients depends on the conjugating plasmid itself. For example, plasmid RP4 can transfer itself between quite distantly related gram negative bacterial while F+ can transfer itself to many fewer, closely related types.

Escherichia coli K12 strain AT2446 that is an Hfr was made doubly lysogenic as described in Part XII of Material and Methods. AT2446 is an HfrH strain and hence transfers its DNA to a recipient starting from 0 minutes. The donor DNA is transferred clockwise with thr (Bachmann, B. J. and K. B. Low, 1980: Linkage map of Escherichia coli K12, edition 6. Microbiol. Rev. 44:1–56) the first bacterial chromosomal marker and malB at 91 minutes about the last. Since the attachment site of bacteriophage λ is at 17 minutes, HfrH should transfer the lysogenic virus (in this case viruses) fairly early and at a high efficiency. When transfer of λ to a non-lysogenic strain occurs, zygotic induction will take place. This phenomenon is the result of the viral genome entering a cytoplasm that lacks the repressor of λ. Without repressor genes, genes begin to express themselves, the phage excises itself from the bacterial chromosome, and the lytic cycle proceeds. This gives rise to approximately 300 genomes of λ per cell and the light genes will be expressed at high levels because of their increased dosage (amount) and because they will also be highly transcribed by the λ promoter $P_L$ which was previously repressed.

Some background light emission will occur in these strains since the luminescence genes will be expressed from their own promoter. We have discovered that the background light can be greatly suppressed by growing the donor strains with sublethal concentrations of streptomycin. It was found that streptomycin selectively inhibits the induction of the luminescent system while almost not affecting the rate of growth. An experiment illustrating the use of conjugation and luminescence is described in Example 6 and as shown in FIG. 7, the amount of light emitted is directly related to the concentration of the recipient cells at a given donor concentration. That the relation between emitted light is linearly related to recipient concentration is illustrated in the insert of FIG. 7. Antibiotics like chloramphenicol (10 μg/ml) and streptomycin (100 μg/ml) totally inhibited the increase in emitted light when they were included during mating.

Using this technique it is possible to determine the presence, the number and the sensitivity to antibiotics of bacteria in a sample. Conjugation is not limited to Hfr's or lysogenic bacteriophages. Any strain can be used which contains a luminescence system, or parts thereof, or other donor genetic system which is absent or poorly expressed in the host organism, in a transferable replicon. The replicon may be the bacterial chromosome or a plasmid. The luminescence system or parts thereof, or other genetic system may be introduced by a bacteriophage or by genetic recombination, either natural or artificial, such that the luminescence or other genes are covalently linked to the transferred genetic material. Thus conjugation is analagous to the use of light coupled transduction and transformation described above.

What is claimed is:

1. A method for detecting and identifying the presence of a target microorganism of interest in a sample suspected of containing one or more unknown microorganisms, comprising the steps of:
   a. preparing by genetic engineering techniques a DNA vector containing a genetic system capable of generating a detectable function,
      (i) said genetic system comprising DNA coding for one or more proteins required for the expression of a detectable function in said target microorganism which function is not a normal metabolic function of said target microorganism or essentially not expressed in said target microorganism; and
      (ii) said vector being capable of the selective introduction of said genetic system into said target microorganism to the exclusion of other microorganisms present in said sample;
   b. exposing said sample to said vector under conditions whereby said vector introduces said genetic system into said target microorganism;
   c. expressing said detectable function in said target microorganism present in said sample; and
   d. detecting expression of said detectable function, the expression of said detectable function indicating the presence and identity of said target microorganism in said sample.

2. A method according to claim 1 wherein said introduced genetic system is a natural or recombinant DNA sequence coding for luciferase luminescent system, beta-galactosidase, alcohol dehydrogenase or other NAD oxidoreductase, transferase, alkaline phosphatase or other hydrolase, lyase, isomerase, or D-trytophan oxidase or other oxidase, and the said introduced genetic system is transferred by conjugation, transformation, or transduction, and said target microorganism to be detected is selected from the genera consisting of Escherichia, aerobacter, Salmonella, Shigella, Klebsiella, Proteus, Pseudomonas, Staphyloccous, Streptococcus, Chlamydia, Mycoplasma, Pneumococcus, Neisseria, Clostridium, Bacillus, Corynebacterium, Mycobacterium, Camphybacter, Vibrio, Serratia, Enterobacter, Providencia, Chromobacterium, Brucella, Yersinia, Haemophilus, and Bordetella.

3. A method according to claim 2 wherein said introduced genetic system comprises a natural or recombinant DNA sequence or functional parts thereof coding for luciferase, derived from a biological source, said target microroganism is a bacterium, and wherein said genetic system is detected in said bacterium by the emission of light, and wherein said genetic system is transferred by transformation or transduction using plasmid or bacteriophage vectors.

4. A method according to claim 3 wherein said genetic system is derived from a microbial source.

5. A method according to claim 4 wherein said genetic system comprises recombinant DNA attached to an expression control sequence capable of effecting the expression of said genetic system in said bacterium.

6. A method according to claim 5 wherein transfer of said genetic system involves transduction and said vector is a bacteriophage comprising recombinant DNA packaged in a capside and said bacteriophage recognizes the genus of said bacterium and subspecies thereof.

7. A method according to claim 6 wherein said bacteriophage is λL28 (ATTCC No.40183), or λL4 or functional mutants thereof.

8. A method according to claim 5 wherein transfer of said genetic system involves transformation and said vector is a plasmid.

9. A method according to claim 8 wherein said transfer vector is pBTK5 or pAChv-1.

10. A method according to any one of claim 3, 4, 5, 6, 7, 8, and 9 wherein said DNA transfer is performed in the presence of autoinducer of the genetic system or functional parts thereof.

11. A method according to claim 10 wherein an aldehyde is added to said sample in which said DNA transfer is carried out.

12. A method according to claim 5 wherein a transposon is used to construct bacteriophage containing all or part of the genetic system.

13. A method according to claim 2 wherein said transfer is effected by conjugation by means of bacterial strains containing said genetic system or functional parts thereof in a transferable replicon, said replicon selected from the group consisting of a bacterial chromosome and a plasmid.

14. A method according to claim 13 wherein the genetic system or functional parts thereof is introduced into said bacterial strain by a bacteriophage.

15. A method according to claim 13 wherein said genetic system or functional parts thereof is introduced into said bacterial strain by natural or artificial genetic recombination.

16. A method according to claim 13 wherein bacterial strains are used that are Hfr's which are lysogenized by temperature bacteriophages carrying the donor DNA system.

17. A method according to claim 1 further comprising transferring said genetic system in the presence of an antibacterial agent and further determining the susceptibility of said target micoorganism to said antibacterial agent.

18. A method according to claim 4 wherein said microbial source is *Vibrio fisheri*.

* * * * *